(12) United States Patent
Gigliotti et al.

(10) Patent No.: US 7,815,918 B2
(45) Date of Patent: Oct. 19, 2010

(54) POLYPEPTIDES AND IMMUNOGENIC CONJUGATES CAPABLE OF INDUCING ANTIBODIES AGAINST PATHOGENS, AND USES THEREOF

(75) Inventors: Francis Gigliotti, Pittsford, NY (US); Terry W. Wright, West Henrietta, NY (US); Constantine G. Haidaris, Rochester, NY (US); Patricia J. Simpsonhaidaris, Rochester, NY (US); Jesse Wells, Rochester, NY (US)

(73) Assignee: University of Rochester, Rochester, NY (US)

( * ) Notice: Subject to any disclaimer, the term of this patent is extended or adjusted under 35 U.S.C. 154(b) by 803 days.

(21) Appl. No.: 10/584,871

(22) PCT Filed: Dec. 31, 2004

(86) PCT No.: PCT/US2004/043959

§ 371 (c)(1),
(2), (4) Date: Dec. 14, 2006

(87) PCT Pub. No.: WO2005/065382

PCT Pub. Date: Jul. 21, 2005

(65) Prior Publication Data

US 2008/0171053 A1 Jul. 17, 2008

Related U.S. Application Data

(60) Provisional application No. 60/533,788, filed on Dec. 31, 2003.

(51) Int. Cl.
*A61K 39/00* (2006.01)
*A61K 39/38* (2006.01)
*A61K 38/00* (2006.01)
*C07K 14/00* (2006.01)

(52) U.S. Cl. .............. 424/274.1; 424/185.1; 424/184.1; 514/2; 530/350; 530/823

(58) Field of Classification Search .................. None
See application file for complete search history.

(56) References Cited

U.S. PATENT DOCUMENTS 6,165,469 A * 12/2000 Mann et al. .............. 424/185.1

FOREIGN PATENT DOCUMENTS

| WO | 95/23513 A1 | 9/1995 |
| WO | WO 98/39424 * | 9/1998 |

OTHER PUBLICATIONS

Gigliotti et al., "Passive Intranasal Monoclonal Antibody Prophylaxis Against Murine *Pneumocystis carinii* Pneumonia," Infection and Immunity 70(3):1069-1074 (2002).
Lee et al., "Molecular Characterization for KEX1, a Kexin-like Protease in Mouse *Pneumocystis carinii*," Gene 242:141-150 (2000).
Wells et al., "Epitope Mapping of a Protective Monoclonal Antibody Against *Pneumocystis carinii* With Shared Reactivity to *Streptococcus pneumoniae* Surface Antigen PspA," Infection and Immunity 72(3):1548-1556 (2004).
Supplemental Partial European Search Report for European Patent Application No. EP04815948 (Jul. 22, 2009).

* cited by examiner

*Primary Examiner*—S. Devi
(74) *Attorney, Agent, or Firm*—Nixon Peabody LLP

(57) ABSTRACT

A number of immunologically active agents are described, including an isolated protein or polypeptide that includes the amino acid sequence of SEQ ID NO: 1, immunogenic conjugates containing either the protein or polypeptide, a full-length *Pneumocystis* kexin, or a full length *Streptococcus pneumoniae* pneumococcal surface protein A (PspA), antibodies recognizing the protein or polypeptide or the immunogenic conjugates (particularly the epitope of SEQ ID NO: 1), and nucleic acid molecules that encode the protein or polypeptide, as well as DNA constructs, expression vectors, and host cells that contain the nucleic acid molecules. Disclosed uses of the antibodies, immunogenic conjugates, and DNA constructs include inducing passive or active immunity to treat or prevent pathogen infections, particularly by a *Pneumocystis* organism, in a patient.

4 Claims, 6 Drawing Sheets

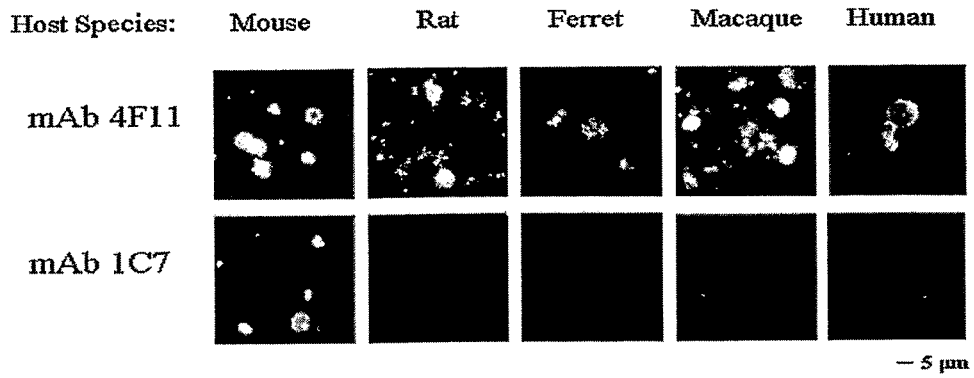

Figure 1

```
        K  P  T  P  Q  P  T  P  Q  P  T  S  E  P  T  S  E  P  T  S  E  P  T  S  E  P  T  P  Q  P  A  P  P  Q  735
2113 AAACCAACACCTCAACCAACACCTCAGCCAACATCTGAGCCAACATCTGAGCCAACATCTGAGCCAACATCTGAACCAACACCTCAACCAGCACCACCTC
        P  A  P  P  Q  P  A  P  Q  P  A  P  Q  P  A  P  Q  P  A  P  Q  P  A  P  P  Q  P  A  P  P  Q  P  V  P  P  Q  P  768
2213 AACCAGCACCACCTCAACCAGCACCTCAACCAGCACCTCAACCAGCACCTCAACCAGCACCACCTCAACCAGCACCACCTCAACCAGTACCACCTCAACC
        V  P  P  Q  P  M  P  S  R  P  A  P  P  K  P  T  P  Q  P  T  S  E  P  A  P  Q  P  T  S  E  S  T  S    801
2313 AGTACCACCTCAACCAATGCCATCTAGACCAGCACCACCTAAACCAACACCTCAACCAACATCTGAGCCAGCACCTCAACCAACATCTGAGTCAACATCT
        E  P  T  P  R  P  P  P  Q  P  T  S  E  P  T  S  E  P  T  S  E  P  S  P  Q  P  T  P  Q  .P 835
2413 GAACCAACACCTCGACCACCACCTCAGCCAACATCTGAGCCAACATCTGAACCAACATCTGAACCAACATCTGAACCATCACCTCAACCAACACCTCAAC
        V  P  Q  P  A  P  Q  P  A  P  P  K  P  A  P  K  P  T  P  P  K  P  A  P  K  P  T  P  P  K  P  A  P  868
2513 CAGTACCTCAACCAGCACCTCAACCAGCACCACCTAAACCGGCACCTAAACCAACACCACCTAAACCGGCACCTAAACCAACACCACCTAAACCAGCGCC
        K  P  A  P  S  K  S  S  S  K  P  T  S  T
2613 TAAACCAGCACCATCTAAATCATCATCTAAACCAACATCTACA
```

Figure 2A

```
        T  N  I  S  E  P  A  L  P  D  K  D  P  Q  P  T  S  S  P  Q  P  K  P  R  P  R  P  R  P  Q  P  Q  P  H  34
  1 ACCAATATATCCGAACCAGCACTGCCTGATAAGGATCCTCAACCTACATCTTCACCTCAGCCAAAACCTCGGCCAAGACCTCGACCTCAACCTCAACCTC
        P  H  P  K  P  Q  P  Q  P  T  P  E  P  Q  P  Q  P  A  P  E  P  R  P  Q  P  T  S  K  P  R  P  Q  P  67
101 ATCCACATCCAAAACCTCAGCCTCAGCCGACGCCAGAACCTCAGCCTCAGCCGGCGCCAGAACCTCGACCTCAGCCGACGTCAAAACCTCGACCTCAGCC
        T  S  K  P  R  P  Q  P  T  P  E  P  R  P  L  P  V  P  G  P  G  P  L  P  V  P  G  P  R  P  Q  P  Q  100
201 AACGTCAAAACCTCGACCTCAGCCGACGCCAGAACCTCGACCTCTGCCGGTGCCAGGACCTGGACCTCTGCCGGTGCCAGGACCTCGACCTCAACCTCAA
        P  Q  P  Q  P  Q  P  Q  P  Q  P  Q  P  Q  P  Q  P  Q  P  Q  P  Q  P  Q  P  Q  P  Q  P  K  P  Q  134
301 CCTCAACCTCAACCTCAGCCTCAACCTCAACCTCAGCCTCAACCTCAACCTCAGCCTCAGCCTCAGCCTCAGCCTCAACCTCAGCCGAAGCCTC
        P  P  S  Q  S  T  S  E  S  A  S  Q  S  K  P  K  P  T  T  Q  T  K  P  S  P  R  P  H  P  K  P  V  P  167
401 AACCACCATCTCAGTCAACATCAGAATCAGCATCGCAATCCAAACCAAAACCAACAACACAAACAAAACCGTCACCGAGACCACACCCAAAGCCGGTGCC
        K  P  S  S  I  D  T  G  P  S  K  S  D  S  S  F  I  F  T  V  T  K  T  I  T  K  I  S  E  T  E  K  P  200
501 AAAACCATCATCGATAGACACAGGACCATCAAAATCGGATTCAAGCTTCATTTTTACAGTAACAAAAACAATAACAAAGATATCAGAAACAGAAAAACCA
        S  T  K  P  S  V  K  P  T  S  T  K  T  T  S  K  P  S  T  K  P  S  T  K  P  S  V  K  P  A  S  T  K  T  234
601 TCTACAAAACCATCTGTGAAACCAACCTCTACAAAGACAACATCAAAACCATCTACAAAACCATCTACAAAACCATCTGTAAAACCAGCCTCTACAAAGA
        T  S  E  S  E  K  P  T  L  E  E  V  P  E  T  K  G  N  G  V  R  V  I  G  F  E  G  L  Q  L  L  S  M  267
701 CAACATCAGAATCAGAAAAACCAACATTGGAAGAAGTTCCAGAAACTAAAGGGAATGGTGTAAGAGTAATAGGATTTGAGGGGTTACAATTATTATCAAT
        I  V  A  I  I  G  I  W  I  M  *
801 GATTGTTGCAATAATAATTGGGATATGGATAATGTAAATTTAATTAGAAGTCATTGGCTATTAAATTAATATATAGTAATTTGTAATAATTAGATAAATA
901 GACAGGGGATCTAGAAATCAATGTGTGATTAAATAAATATAAAAATCTAAAAAAAAAAAAAAAAAAA
```

Figure 2B

| Construct | Sequence of insert |
|---|---|
| KEXIN$_{856-872}$ | KPAPKPTPPKPAPKPAP |
| KEXIN$_{856-863}$ | KPAPKPTP |
| KEXIN$_{865-872}$ | KPAPKPAP |
| KEXIN$_{860-868}$ | KPTPPKPAP |
| KEXIN$_{777-787}$ | RPAPPKPTPQP |
| A12$_{46-53}$ | EPQPQPAP |
| A12$_{54-61}$ | EPRPQPTS |
| A12$_{70-77}$ | KPRPQPTP |
| A12$_{62-77}$ | KPRPQPTS-KPRPQPTP |

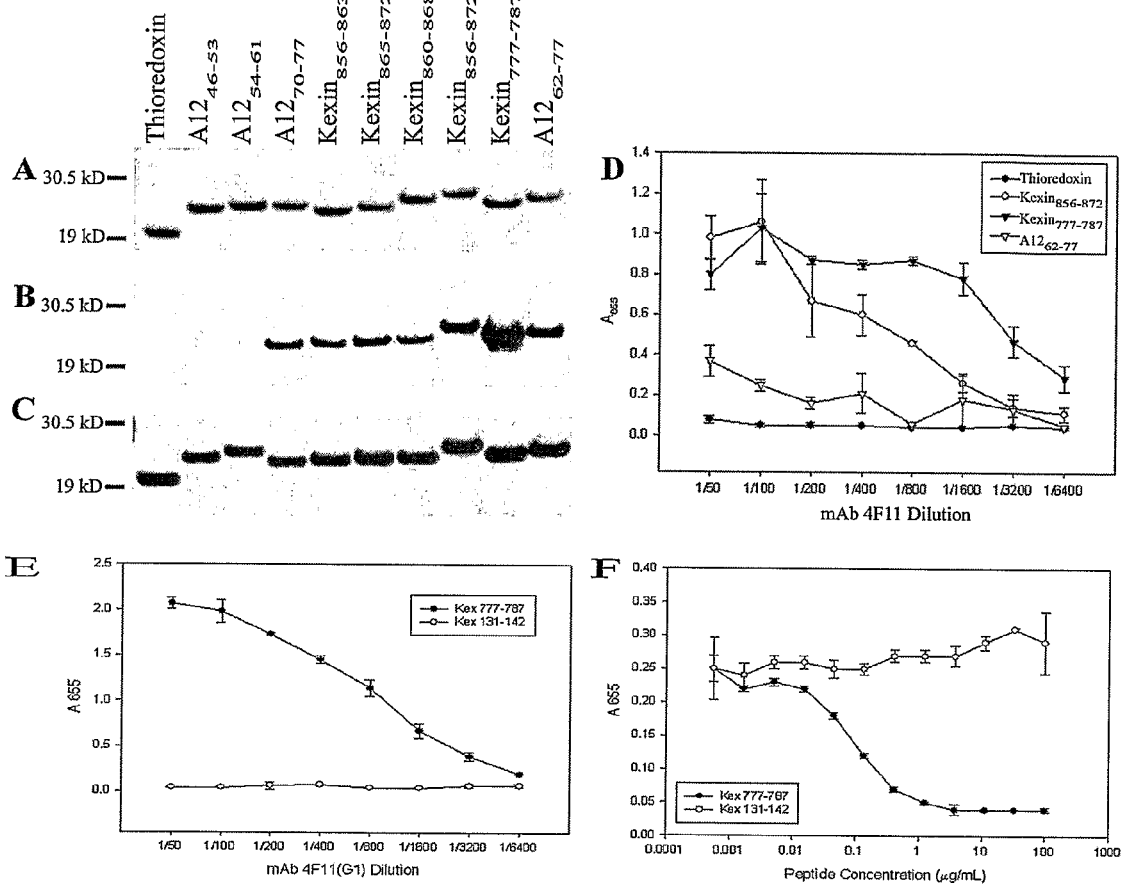
Figures 5A-F

```
URSP2 PspA    EKELKEIDESDSEDYIKEGLRAPLQSKLDAKKAKLSKLEELSDKIDEL          280

URSP2 PspA    DAEIAKLEKDVEDFKNSDGEQAEQYLVAAKKDLDAKKAELENTEADLK          328

Kex856-872                              KPAPKPTP.PKPAPKPAP
                                        ||||| | ||||| |||
URSP2 PspA    KAVDEPETPAPAPKPAPAPAPTPEAPAPAPKPAPAPKPAPAPAPTPEA          376
                                        :||| ||| | |
Kex777-787                              RPAP.PKPTPQP

Kex856-872           KPAPKPTP.PKPAPKPAP
                     ||||| | ||||| |||
URSP2 PspA    PAPAPKPAPAPKPAPAPAPTPEAPAPAPKPAPAPRPAPAPKPAPDPKP          424
                     :||| ||| | |                  |||| ||| | |
Kex777-787           RPAP.PKPTPQP                  RPAP.PKPTPQP
```

Figure 6

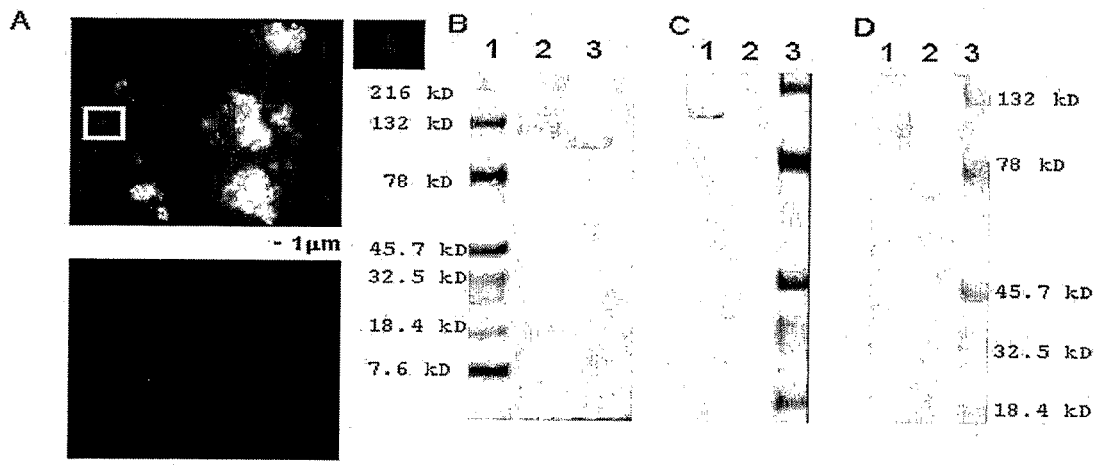

Figures 7A-D

```
1                    21                   41                   61                   81
|                    |                    |                    |                    |
CTAGATACTCGTGCTAATGTATTTTCTTCATGTTATAAAGAAGATATGGATTTTTCAGCCAAATTAGATCTTCTAAATAGGATAAAAGAT
 L  D  T  R  A  N  V  F  S  S  C  Y  K  E  D  M  D  F  S  A  K  L  D  L  L  N  R  I  K  D 101                  121                  141                  161
          |                    |                    |                    |
AAGATTGTAGTTCCAAAAGGAAACACGAGGTATTTTGTAGAGTTATTGTGTAAAAGCTATATTGTCGCCGAATGCAGCGCCAGTGATTTA
 K  I  V  V  P  K  G  N  T  R  Y  F  V  E  L  L  C  K  S  Y  I  V  A  E  C  S  A  S  D  L 181                  201                  221                  241                  261
 |                    |                    |                    |                    |
ATGTTCAAATCTTATGCTCTTATGGAAGCCTGTCTTCACCCAGAAAGGATCTGTAGAGAATTAAAAAATCATTTTTCCGAAGAATCTAGG
 M  F  K  S  Y  A  L  M  E  A  C  L  H  P  E  R  I  C  R  E  L  K  N  H  F  S  E  E  S  R 281                  301                  321                  341
              |                    |                    |                    |
AAATTAGAAAATAAATTAAGGAGTATTTTAAAACCCACATATTATGAATGCAAAGATCTAGGACAAAAGTGCAACTCTGGATTTTATTTT
 K  L  E  N  K  L  R  S  I  L  K  P  T  Y  Y  E  C  K  D  L  G  Q  K  C  N  S  G  F  Y  F 361                  381                  401                  421                  441
 |                    |                    |                    |                    |
GATGGAGATATAGAAGCTCAATGCAATCATTTCAAAAAAAGATGTCAAGATAAACAAGAGACTAAAATTAATTAATCATATTGTTGAT
 D  G  D  I  E  A  Q  C  N  H  F  K  K  R  C  Q  D  K  Q  E  R  L  K  L  I  N  H  I  V  D 461                  481                  501                  521
              |                    |                    |                    |
TCATCTGCTCTTTATCTCGCAAATGAAGTACAATGCAGAACTTATTTCGACAGTTTTTGTGGTGCGAATGTAAAACAAGAATTCAAACAA
 S  S  A  L  Y  L  A  N  E  V  Q  C  R  T  Y  F  D  S  F  C  G  A  N  V  K  Q  E  F  K  Q 541                  561                  581                  601                  621
 |                    |                    |                    |                    |
ATATGCAACAAAGGAGCTAATGGCATATGCCCTGATATAATAGATGATTCTAAAGAACATTGTGCTCATTTGATTAATCATTTAACATCT
 I  C  N  K  G  A  N  G  I  C  P  D  I  I  D  D  S  K  E  H  C  A  H  L  I  N  H  L  T  S 641                  661                  681                  701
              |                    |                    |                    |
CTTGGAATTTCATCGTCTTCTGCTTCACTTCCATTGGACTATTGCGACTCAGCGATTAATTACTGTAATTCTCTTTCGAAGTTTTGCACG
 L  G  I  S  S  S  S  A  S  L  P  L  D  Y  C  D  S  A  I  N  Y  C  N  S  L  S  K  F  C  T 721                  741                  761                  781                  801
 |                    |                    |                    |                    |
GAATCAAAACGACAGTGCGATTCTGTTATTTCTTTCTGCACTAGCGAATCAAAAAAAACTGATGAATATGGTTCTTTTATTGACCAATAT
 E  S  K  R  Q  C  D  S  V  I  S  F  C  T  S  E  S  K  K  T  D  E  Y  G  S  F  I  D  Q  Y 821                  841                  861                  881
              |                    |                    |                    |
CCCGCGGCTGCAGCAAATGCAACCAAATGCAAGGTAACTTTGAAAGAGTTATGCCAAGATTCAAGCAAAAAAGACTCTTATTCAACACTA
 P  A  A  A  A  N  A  T  K  C  K  V  T  L  K  E  L  C  Q  D  S  S  K  K  D  S  Y  S  T  L 901                  921                  941                  961                  981
 |                    |                    |                    |                    |
TGTGCTTATAATAAAGATGGTTATACCGAAATATGTAAAAACTTAAGAAATTTCATAGAAAAAGCATGCGAGAATTTGAGAATTCATTTA
 C  A  Y  N  K  D  G  Y  T  E  I  C  K  N  L  R  N  F  I  E  K  A  C  E  N  L  R  I  H  L 1001                 1021                 1041                 1061
              |                    |                    |                    |
CATACTTATGATACAAACTCACTCAATACGAATAAAGGATCTGCTCAAGATAGATGCACTTATATAAGAAATCTTTACTTTAAATTTAAA
 H  T  Y  D  T  N  S  L  N  T  N  K  G  S  A  Q  D  R  C  T  Y  I  R  N  L  Y  F  K  F  K 1081                 1101                 1121                 1141                 1161
 |                    |                    |                    |                    |
AATATATGTTTATTGGTTGATCCTTTCTATGACTTATCTCCTATTATCACTCAAGAATGTAAAACCAATATATCCGAACCAGCACTGCCT
 N  I  C  L  L  V  D  P  F  Y  D  L  S  P  I  I  T  Q  E  C  K  T  N  I  S  E  P  A  L  P 1181                 1201                 1221                 1241
              |                    |                    |                    |
GATAAGGATCCTCAACCTACATCTTCACCCTCAGCCAAAACCTCGGCCAAGACCTCGACCTCAACCTCAACCTCATCCACATCCAAAACCT
 D  K  D  P  Q  P  T  S  S  P  Q  P  K  P  R  P  R  P  R  P  Q  P  Q  P  H  P  H  P  K  P
```

Figure 8A

```
1261                1281                1301                1321                1341
 |                   |                   |                   |                   |
CAGCCTCAGCCGACGCCAGAACCTCAGCCTCAGCCGGCGCCAGAACCTCGACCTCAGCCGACGTCAAAACCTCGACCTCAGCCAACGTCA
 Q  P  Q  P  T  P  E  P  Q  P  Q  P  A  P  E  P  R  P  Q  P  T  S  K  P  R  P  Q  P  T  S 1361                1381                1401                1421
         |                   |                   |                   |
AAACCTCGACCTCAGCCGACGCCAGAACCTCGACCTCTGCCGGTGCCAGGACCTGGACCTCTGCCGGTGCCAGGACCTCGACCTCAACCT
 K  P  R  P  Q  P  T  P  E  P  R  P  L  P  V  P  G  P  L  P  V  P  G  R  P  Q  P 1441                1461                1481                1501                1521
 |                   |                   |                   |                   |
CAACCTCAACCTCAACCTCAGCCTCAACCTCAACCTCAGCCTCAACCTCAACCTCAGCCTCAGCCTCAGCCTCAGCCTCAGCCTCAACCT
 Q  P  Q  P  Q  P  Q  P  Q  P  Q  P  Q  P  Q  P  Q  P  Q  P  Q  P  Q  P  Q  P 1541                1561                1581                1601
         |                   |                   |                   |
CAGCCGAAGCCTCAACCACCATCTCAGTCAACATCAGAATCAGCATCGCAATCCAAACCAAAACCAACAACACAAACAAAACCGTCACCG
 Q  P  K  P  Q  P  P  S  Q  S  T  S  E  S  A  S  Q  S  K  P  K  P  T  T  Q  T  K  P  S  P 1621                1641                1661                1681                1701
 |                   |                   |                   |                   |
AGACCACACCCAAAGCCGGTGCCAAAACCATCATCGATAGACACAGGACCATCAAAATCGGATTCAAGCTTCATTTTTACAGTAACAAAA
 R  P  H  P  K  P  V  P  K  P  S  S  I  D  T  G  P  S  K  S  D  S  S  F  I  F  T  V  T  K 1721                1741                1761                1781
         |                   |                   |                   |
ACAATAACAAAGATATCAGAAACAGAAAAACCATCTACAAAACCATCTGTGAAACCAACCTCTACAAAGACAACATCAAAACCATCTACA
 T  I  T  K  I  S  E  T  E  K  P  S  T  K  P  S  V  K  P  T  S  T  K  T  T  S  K  P  S  T 1801                1821                1841                1861                1881
 |                   |                   |                   |                   |
AAACCATCTACAAAACCATCTGTAAAACCAGCCTCTACAAAGACAACATCAGAATCAGAAAAACCAACATTGGAAGAAGTTCCAGAAACT
 K  P  S  T  K  P  S  V  K  P  A  S  T  K  T  T  S  E  S  E  K  P  T  L  E  E  V  P  E  T 1901                1921                1941                1961
         |                   |                   |                   |
AAAGGGAATGGTGTAAGAGTAATAGGATTTGAGGGGTTACAATTATTATCAATGATTGTTGCAATAATAATTGGGATATGGATAATGTAA
 K  G  N  G  V  R  V  I  G  F  E  G  L  Q  L  L  S  M  I  V  A  I  I  I  G  I  W  I  M  -
```

Figure 8B

SEQUENCE LISTING

<160> NUMBER OF SEQ ID NOS: 67

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (1)
<223> OTHER INFORMATION: Xaa at position 1 is Arg, Lys, or Gln
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (5)
<223> OTHER INFORMATION: Xaa at position 5 is optional and can be Pro
<220> FEATURE:
<221> NAME/KEY: PEPTIDE
<222> LOCATION: (6)
<223> OTHER INFORMATION: Xaa at position 6 is Lys, Gln, or Arg
<220> FEATURE:
<221> NAME/KEY: PEPTIDE
<222> LOCATION: (8)
<223> OTHER INFORMATION: Xaa at position 8 is any amino acid

<400> SEQUENCE: 1

Xaa Pro Xaa Pro Xaa Xaa Pro Xaa Pro
 1               5

<210> SEQ ID NO 2
<211> LENGTH: 543
<212> TYPE: DNA
<213> ORGANISM: Artificial Sequence
<220> FEATURE:
<223> OTHER INFORMATION: Description of Artificial Sequence: partial
      nucleotide sequence of the proline rich domain of
      mouse P. carinii kexin

<400> SEQUENCE: 2
aaaccaacac ctcaaccaac acctcagcca acatctgagc caacatctga gccaacatct      60
gagccaacat ctgaaccaac acctcaacca gcaccacctc aaccagcacc acctcaacca     120
gcacctcaac cagcacctca accagcacct caaccagcac acctcaacc agcaccacct     180 caaccagtac cacctcaacc agtaccacct caaccaatgc catctagacc agcaccacct     240
aaaccaacac ctcaaccaac atctgagcca gcacctcaac caacatctga gtcaacatct     300
gaaccaacac ctcgaccacc acctcagcca acatctgagc caacatctga accaacatct     360
gaaccaacat ctgaaccatc acctcaacca acacctcaac cagtacctca accagcacct     420
caaccagcac cacctaaacc ggcacctaaa ccaacaccac ctaaaccggc acctaaacca     480
acaccaccta aaccagcgcc taaaccagca ccatctaaat catcatctaa accaacatct     540
aca                                                                   543

<210> SEQ ID NO 3
<211> LENGTH: 181
<212> TYPE: PRT
<213> ORGANISM: Artificial Sequence
<220> FEATURE:
<223> OTHER INFORMATION: Description of Artificial Sequence: deduced
      amino acid sequence of the proline rich domain of mouse
      P. carinii kexin

<400> SEQUENCE: 3

| Lys | Pro | Thr | Pro | Gln | Pro | Thr | Pro | Gln | Pro | Thr | Ser | Glu | Pro | Thr | Ser |
|---|---|---|---|---|---|---|---|---|---|---|---|---|---|---|---|
| 1 | | | | 5 | | | | | 10 | | | | | 15 | |

| Glu | Pro | Thr | Ser | Glu | Pro | Thr | Ser | Glu | Pro | Thr | Pro | Gln | Pro | Ala | Pro |
|---|---|---|---|---|---|---|---|---|---|---|---|---|---|---|---|
| | | | 20 | | | | | 25 | | | | | 30 | | |

| Pro | Gln | Pro | Ala | Pro | Pro | Gln | Pro | Ala | Pro | Gln | Pro | Ala | Pro | Gln | Pro |
|---|---|---|---|---|---|---|---|---|---|---|---|---|---|---|---|
| | | 35 | | | | | 40 | | | | | 45 | | | |

| Ala | Pro | Gln | Pro | Ala | Pro | Pro | Gln | Pro | Ala | Pro | Pro | Gln | Pro | Val | Pro |
|---|---|---|---|---|---|---|---|---|---|---|---|---|---|---|---|
| | 50 | | | | | 55 | | | | | 60 | | | | |

| Pro | Gln | Pro | Val | Pro | Pro | Gln | Pro | Met | Pro | Ser | Arg | Pro | Ala | Pro | Pro |
|---|---|---|---|---|---|---|---|---|---|---|---|---|---|---|---|
| 65 | | | | | 70 | | | | | 75 | | | | | 80 |

| Lys | Pro | Thr | Pro | Gln | Pro | Thr | Ser | Glu | Pro | Ala | Pro | Gln | Pro | Thr | Ser |
|---|---|---|---|---|---|---|---|---|---|---|---|---|---|---|---|
| | | | | 85 | | | | | 90 | | | | | 95 | |

| Glu | Ser | Thr | Ser | Glu | Pro | Thr | Pro | Arg | Pro | Pro | Pro | Gln | Pro | Thr | Ser |
|---|---|---|---|---|---|---|---|---|---|---|---|---|---|---|---|
| | | | 100 | | | | | 105 | | | | | 110 | | |

| Glu | Pro | Thr | Ser | Glu | Pro | Thr | Ser | Glu | Pro | Thr | Ser | Glu | Pro | Ser | Pro |
|---|---|---|---|---|---|---|---|---|---|---|---|---|---|---|---|
| | | | | 115 | | | | | 120 | | | | | 125 | |

| Gln | Pro | Thr | Pro | Gln | Pro | Val | Pro | Gln | Pro | Ala | Pro | Gln | Pro | Ala | Pro |
|---|---|---|---|---|---|---|---|---|---|---|---|---|---|---|---|
| | 130 | | | | | 135 | | | | | 140 | | | | |

| Pro | Lys | Pro | Ala | Pro | Lys | Pro | Thr | Pro | Pro | Lys | Pro | Ala | Pro | Lys | Pro |
|---|---|---|---|---|---|---|---|---|---|---|---|---|---|---|---|
| 145 | | | | | 150 | | | | | 155 | | | | | 160 |

| Thr | Pro | Pro | Lys | Pro | Ala | Pro | Lys | Pro | Ala | Pro | Ser | Lys | Ser | Ser | Ser |
|---|---|---|---|---|---|---|---|---|---|---|---|---|---|---|---|
| | | | | 165 | | | | | 170 | | | | | 175 | |

| Lys | Pro | Thr | Ser | Thr |
|---|---|---|---|---|
| | | | | 180 |

<210> SEQ ID NO 4
<211> LENGTH: 967
<212> TYPE: DNA
<213> ORGANISM: Artificial Sequence
<220> FEATURE:
<223> OTHER INFORMATION: Description of Artificial Sequence: nucleotide sequence of P. carinii cDNA clone A12

<400> SEQUENCE: 4

```
accaatatat ccgaaccagc actgcctgat aaggatcctc aacctacatc ttcacctcag    60
ccaaaacctc ggccaagacc tcgacctcaa cctcaacctc atccacatcc aaaacctcag   120
cctcagccga cgccagaacc tcagcctcag ccggcgccag aacctcgacc tcagccgacg   180
tcaaaacctc gacctcagcc aacgtcaaaa cctcgacctc agccgacgcc agaacctcga   240
cctctgccgg tgccaggacc tggacctctg ccggtgccag gacctcgacc tcaacctcaa   300
cctcaacctc aacctcagcc tcaacctcaa cctcagcctc aacctcaacc tcagcctcag   360
cctcagcctc agcctcagcc tcaacctcag ccgaagcctc aaccaccatc tcagtcaaca   420
tcagaatcag catcgcaatc caaaccaaaa ccaacaacac aaacaaaacc gtcaccgaga   480
ccacacccaa agccggtgcc aaaaccatca tcgatagaca caggaccatc aaaatcggat   540
tcaagcttca tttttacagt aacaaaaaca ataacaaaga tatcagaaac agaaaaacca   600
tctacaaaac catctgtgaa accaacctct acaaagacaa catcaaaacc atctacaaaa   660
ccatctacaa aaccatctgt aaaaccagcc tctacaaaga caacatcaga atcagaaaaa   720
ccaacattgg aagaagttcc agaaactaaa gggaatggtg taagagtaat aggatttgag   780
gggttacaat tattatcaat gattgttgca ataataattg ggatatggat aatgtaaatt   840
taattagaag tcattggcta ttaaattaat atatagtaat ttgtaataat tagataaata   900
```

-continued

```
gacaggggat ctagaaatca atgtgtgatt aaataaatat aaaaatctaa aaaaaaaaa    960 aaaaaaa                                                              967
```

<210> SEQ ID NO 5
<211> LENGTH: 278
<212> TYPE: PRT
<213> ORGANISM: Artificial Sequence
<220> FEATURE:
<223> OTHER INFORMATION: Description of Artificial Sequence: amino
    acid sequence of P. carinii cDNA clone A12

<400> SEQUENCE: 5

```
Thr Asn Ile Ser Glu Pro Ala Leu Pro Asp Lys Asp Pro Gln Pro Thr
 1               5                  10                  15

Ser Ser Pro Gln Pro Lys Pro Arg Pro Arg Pro Gln Pro Gln
            20                  25                  30

Pro His Pro His Pro Lys Pro Gln Pro Gln Pro Thr Pro Glu Pro Gln
        35                  40                  45

Pro Gln Pro Ala Pro Glu Pro Arg Pro Gln Pro Thr Ser Lys Pro Arg
    50                  55                  60

Pro Gln Pro Thr Ser Lys Pro Arg Pro Gln Pro Thr Pro Glu Pro Arg
65                  70                  75                  80

Pro Leu Pro Val Pro Gly Pro Gly Pro Leu Pro Val Pro Gly Pro Arg
                85                  90                  95

Pro Gln Pro Gln Pro Gln Pro Gln Pro Gln Pro Gln Pro Gln Pro Gln
            100                 105                 110

Pro Gln Pro Gln Pro Gln Pro Gln Pro Gln Pro Gln Pro Gln Pro Gln
        115                 120                 125

Pro Gln Pro Lys Pro Gln Pro Pro Ser Gln Ser Thr Ser Glu Ser Ala
    130                 135                 140

Ser Gln Ser Lys Pro Lys Pro Thr Thr Gln Thr Lys Pro Ser Pro Arg
145                 150                 155                 160

Pro His Pro Lys Pro Val Pro Lys Pro Ser Ser Ile Asp Thr Gly Pro
                165                 170                 175

Ser Lys Ser Asp Ser Ser Phe Ile Phe Thr Val Thr Lys Thr Ile Thr
            180                 185                 190

Lys Ile Ser Glu Thr Glu Lys Pro Ser Thr Lys Pro Ser Val Lys Pro
        195                 200                 205

Thr Ser Thr Lys Thr Thr Ser Lys Pro Ser Thr Lys Pro Ser Thr Lys
    210                 215                 220

Pro Ser Val Lys Pro Ala Ser Thr Lys Thr Thr Ser Glu Ser Glu Lys
225                 230                 235                 240

Pro Thr Leu Glu Glu Val Pro Glu Thr Lys Gly Asn Gly Val Arg Val
                245                 250                 255

Ile Gly Phe Glu Gly Leu Gln Leu Leu Ser Met Ile Val Ala Ile Ile
            260                 265                 270

Ile Gly Ile Trp Ile Met
        275
```

<210> SEQ ID NO 6
<211> LENGTH: 192
<212> TYPE: PRT
<213> ORGANISM: Artificial Sequence
<220> FEATURE:
<223> OTHER INFORMATION: Description of Artificial Sequence: partial
    deduced amino acid sequence of S. pneumoniae URSP2
    PspA

```
<400> SEQUENCE: 6

Glu Lys Glu Leu Lys Glu Ile Asp Glu Ser Asp Ser Glu Asp Tyr Ile
 1               5                  10                  15

Lys Glu Gly Leu Arg Ala Pro Leu Gln Ser Lys Leu Asp Ala Lys Lys
             20                  25                  30

Ala Lys Leu Ser Lys Leu Glu Glu Leu Ser Asp Lys Ile Asp Glu Leu
         35                  40                  45

Asp Ala Glu Ile Ala Lys Leu Glu Lys Asp Val Glu Asp Phe Lys Asn
     50                  55                  60

Ser Asp Gly Glu Gln Ala Glu Gln Tyr Leu Val Ala Ala Lys Lys Asp
 65                  70                  75                  80

Leu Asp Ala Lys Lys Ala Glu Leu Glu Asn Thr Glu Ala Asp Leu Lys
                 85                  90                  95

Lys Ala Val Asp Glu Pro Glu Thr Pro Ala Pro Ala Pro Lys Pro Ala
             100                 105                 110

Pro Ala Pro Ala Pro Thr Pro Glu Ala Pro Ala Pro Ala Pro Lys Pro
             115                 120                 125

Ala Pro Ala Pro Lys Pro Ala Pro Ala Pro Thr Pro Glu Ala
130                 135                 140

Pro Ala Pro Ala Pro Lys Pro Ala Pro Ala Pro Lys Pro Ala Pro Ala
145                 150                 155                 160

Pro Ala Pro Thr Pro Glu Ala Pro Ala Pro Ala Pro Lys Pro Ala Pro
             165                 170                 175

Ala Pro Arg Pro Ala Pro Ala Pro Lys Pro Ala Pro Asp Pro Lys Pro
             180                 185                 190

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 7

Arg Pro Xaa Pro Pro Lys Pro Xaa Pro
 1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 8

Arg Pro Xaa Pro Pro Gln Pro Xaa Pro
 1               5
```

```
<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 9

Arg Pro Xaa Pro Pro Arg Pro Xaa Pro
 1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 10

Lys Pro Xaa Pro Pro Lys Pro Xaa Pro
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 11

Lys Pro Xaa Pro Pro Gln Pro Xaa Pro
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid
```

```
<400> SEQUENCE: 12

Lys Pro Xaa Pro Pro Arg Pro Xaa Pro
  1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 13

Gln Pro Xaa Pro Pro Lys Pro Xaa Pro
  1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 14

Gln Pro Xaa Pro Pro Gln Pro Xaa Pro
  1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (8)
<223> OTHER INFORMATION: Xaa at position 8 is any amino acid

<400> SEQUENCE: 15

Gln Pro Xaa Pro Pro Arg Pro Xaa Pro
  1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
```

```
<220> FEATURE:
<221> NAME/KEY: PEPTIDE
<222> LOCATION: (7)
<223> OTHER INFORMATION: Xaa at position 7 is any amino acid

<400> SEQUENCE: 16

Arg Pro Xaa Pro Lys Pro Xaa Pro
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 17

Arg Pro Xaa Pro Gln Pro Xaa Pro
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 18

Arg Pro Xaa Pro Arg Pro Xaa Pro
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence:  peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 19

Lys Pro Xaa Pro Lys Pro Xaa Pro
 1               5

<210> SEQ ID NO 20
<211> LENGTH: 8
<212> TYPE: PRT
<213> ORGANISM: Artificial Sequence
```

```
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 20

Lys Pro Xaa Pro Gln Pro Xaa Pro
  1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 21

Lys Pro Xaa Pro Arg Pro Xaa Pro
  1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 22

Gln Pro Xaa Pro Lys Pro Xaa Pro
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 23

Gln Pro Xaa Pro Gln Pro Xaa Pro
  1               5
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: peptide
<220> FEATURE:
<221> NAME/KEY: PEPTIDE
<222> LOCATION: (3)
<223> OTHER INFORMATION: Xaa at position 3 is any amino acid
<220> FEATURE:
<221> NAME/KEY: PEPTIDE
<222> LOCATION: (7)
<223> OTHER INFORMATION: Xaa at position 7 is any amino acid

<400> SEQUENCE: 24

Gln Pro Xaa Pro Arg Pro Xaa Pro
 1               5

<210> SEQ ID NO 25
<211> LENGTH: 52
<212> TYPE: DNA
<213> ORGANISM: Artificial Sequence
<220> FEATURE:
<223> OTHER INFORMATION: Description of Artificial Sequence: Kexin
      Epitope S

<400> SEQUENCE: 25
aaaccggcac ctaaaccaac accacctaaa ccagcgccta aaccagcacc aa          52

<210> SEQ ID NO 26
<211> LENGTH: 52
<212> TYPE: DNA
<213> ORGANISM: Artificial Sequence
<220> FEATURE:
<223> OTHER INFORMATION: Description of Artificial Sequence: Kexin
      Epitope AS

<400> SEQUENCE: 26
tggtgctggt ttaggcgctg gtttaggtgg tgttggttta ggtgccggtt ta          52

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: A39
      Epitope2 S

<400> SEQUENCE: 27
agaccagcac cacctaaacc aacacctcaa ccaa                              34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: A39
      Epitope2 AS

<400> SEQUENCE: 28
tggttgaggt gttggtttag gtggtgctgg tcta                              34

<210> SEQ ID NO 29
<211> LENGTH: 25
<212> TYPE: DNA
<213> ORGANISM: Artificial Sequence
```

```
<220> FEATURE:
<223> OTHER INFORMATION: Description of Artificial Sequence: A32.1
      Epitope S

<400> SEQUENCE: 29
aaaccggcac ctaaaccaac accaa                                          25

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: A32.1
      Epitope AS

<400> SEQUENCE: 30
tggtgttggt ttaggtgccg gttta                                          25

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: A32.2
      Epitope S

<400> SEQUENCE: 31
aaaccagcgc ctaaaccagc accaa                                          25

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: A32.2
      Epitope AS

<400> SEQUENCE: 32
tggtgctggt ttaggcgctg gttta                                          25

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: A32.3
      Epitope S

<400> SEQUENCE: 33
aaaccaacac cacctaaacc agcgccta                                       28

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: A32.3
      Epitope AS

<400> SEQUENCE: 34
aggcgctggt ttaggtggtg ttggttta                                       28

<210> SEQ ID NO 35
<211> LENGTH: 21
<212> TYPE: DNA
<213> ORGANISM: Artificial Sequence
```

```
<220> FEATURE:
<223> OTHER INFORMATION: Description of Artificial Sequence: pSCREEN
      T7 10 S

<400> SEQUENCE: 35
ctgggtaagg agattattgc g                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: A32
      Epitope AS2

<400> SEQUENCE: 36
tggtgctggt ttaggcgctg g                                              21

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: A32
      Epitope S3

<400> SEQUENCE: 37
tctaaatcat catctaaacc aacatc                                         26

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: pSCREEN
      T7 10 AS

<400> SEQUENCE: 38
cgcaagcttg tcgacggag                                                 19

<210> SEQ ID NO 39
<211> LENGTH: 49
<212> TYPE: DNA
<213> ORGANISM: Artificial Sequence
<220> FEATURE:
<223> OTHER INFORMATION: Description of Artificial Sequence: A12
      Epitope S

<400> SEQUENCE: 39
aaacctcgac ctcagccaac gtcaaaacct cgacctcagc cgacgccaa                49

<210> SEQ ID NO 40
<211> LENGTH: 49
<212> TYPE: DNA
<213> ORGANISM: Artificial Sequence
<220> FEATURE:
<223> OTHER INFORMATION: Description of Artificial Sequence: A12
      Epitope AS

<400> SEQUENCE: 40
tggcgtcggc tgaggtcgag gttttgacgt tggctgaggt cgaggttta               49

<210> SEQ ID NO 41
<211> LENGTH: 25
<212> TYPE: DNA
<213> ORGANISM: Artificial Sequence
```

-continued

<220> FEATURE:
<223> OTHER INFORMATION: Description of Artificial Sequence: A12.2
      Epitope S

<400> SEQUENCE: 41
aaacctcgac ctcagccgac gccaa                                                25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: A12.2
      Epitope AS

<400> SEQUENCE: 42
tggcgtcggc tgaggtcgag gttta                                                25

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: A12'2
      Epitope S

<400> SEQUENCE: 43
gaacctcgac ctcagccgac gtcaa                                                25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: A12'2
      Epitope AS

<400> SEQUENCE: 44
tgacgtcggc tgaggtcgag gttca                                                25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: A12'3
      Epitope S

<400> SEQUENCE: 45
gaacctcagc ctcagccggc gccaa                                                25

<210> SEQ ID NO 46
<211> LENGTH: 25
<212> TYPE: DNA
<213> ORGANISM: Artificial Sequence
<220> FEATURE:
<223> OTHER INFORMATION: Description of Artificial Sequence: A12'3
      Epitope AS

<400> SEQUENCE: 46
tggcgccggc tgaggctgag gttca                                                25

<210> SEQ ID NO 47
<211> LENGTH: 20
<212> TYPE: DNA
<213> ORGANISM: Artificial Sequence

```
<220> FEATURE:
<223> OTHER INFORMATION: Description of Artificial Sequence:  A12 S

<400> SEQUENCE: 47
accaatatat ccgaaccagc                                              20

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence:  A12 Mid AS

<400> SEQUENCE: 48
ttctgatgtt gactgagatg g                                            21

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence:  A12 Mid
      AS2

<400> SEQUENCE: 49
ccgacgccag aacctcg                                                 17

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence:  Lambda
      forward

<400> SEQUENCE: 50
tggcgacgac tcctggagcc cg                                           22

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:  Lambda
      reverse

<400> SEQUENCE: 51
tgacaccaga ccaactggta atgg                                         24

<210> SEQ ID NO 52
<211> LENGTH: 28
<212> TYPE: DNA
<213> ORGANISM: Artificial Sequence
<220> FEATURE:
<223> OTHER INFORMATION: Description of Artificial Sequence:  PspA S2

<400> SEQUENCE: 52
gcaagcttat gatatagaaa tttgtaac                                     28

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence:  PspA AS
```

-continued

```
<400> SEQUENCE: 53
ccacataccg ttttcttgtt tccagcc                                              27

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence:  PspA S3

<400> SEQUENCE: 54
acaagtctag ccagctcgc                                                       19

<210> SEQ ID NO 55
<211> LENGTH: 27
<212> TYPE: DNA
<213> ORGANISM: Artificial Sequence
<220> FEATURE:
<223> OTHER INFORMATION: Description of Artificial Sequence:  PspA AS

<400> SEQUENCE: 55
ccacataccg ttttcttgtt tccagcc                                              27

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence:  mouse P.
      carinii kexin fragment 777-787

<400> SEQUENCE: 56

Arg Pro Ala Pro Pro Lys Pro Thr Pro Gln Pro
 1               5                  10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence:  mouse P.
      carinii kexin fragment 131-142

<400> SEQUENCE: 57

Ser Gly Asp Thr Gly Asn Val Asn Ser Gly Glu Lys
 1               5                  10

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence:  mouse P.
      carinii kexin fragment 856-872

<400> SEQUENCE: 58

Lys Pro Ala Pro Lys Pro Thr Pro Pro Lys Pro Ala Pro Lys Pro Ala
 1               5                  10                  15

Pro

<210> SEQ ID NO 59
<211> LENGTH: 16
<212> TYPE: PRT
<213> ORGANISM: Artificial Sequence
```

```
<220> FEATURE:
<223> OTHER INFORMATION: Description of Artificial Sequence: mouse P.
      carinii clone A12 fragment 62-77

<400> SEQUENCE: 59

Lys Pro Arg Pro Gln Pro Thr Ser Lys Pro Arg Pro Gln Pro Thr Pro
 1               5                   10                  15

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: mouse P.
      carinii kexin fragment 856-863

<400> SEQUENCE: 60

Lys Pro Ala Pro Lys Pro Thr Pro
 1               5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: mouse P.
      carinii kexin fragment 865-872

<400> SEQUENCE: 61

Lys Pro Ala Pro Lys Pro Ala Pro
 1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: mouse P.
      carinii kexin fragment 860-868

<400> SEQUENCE: 62

Lys Pro Thr Pro Pro Lys Pro Ala Pro
 1               5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: mouse P.
      carinii clone A12 fragment 70-77

<400> SEQUENCE: 63

Lys Pro Arg Pro Gln Pro Thr Pro
 1               5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: mouse P.
      carinii clone A12 fragment 46-53

<400> SEQUENCE: 64

Glu Pro Arg Pro Gln Pro Thr Ser
 1               5
```

```
<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: mouse P.
      carinii clone A12 fragment 54-61

<400> SEQUENCE: 65

Glu Pro Gln Pro Gln Pro Ala Pro
  1               5

<210> SEQ ID NO 66
<211> LENGTH: 1980
<212> TYPE: DNA
<213> ORGANISM: Artificial Sequence
<220> FEATURE:
<223> OTHER INFORMATION: Description of Artificial Sequence: partial
      nucleotide sequence of P. carinii cDNA clone A12

<400> SEQUENCE: 66
ctagatactc gtgctaatgt attttcttca tgttataaag aagatatgga ttttcagcc      60 aaattagatc ttctaaatag gataaaagat aagattgtag ttccaaaagg aaacacgagg    120
tattttgtag agttattgtg taaaagctat attgtcgccg aatgcagcgc cagtgattta    180
atgttcaaat cttatgctct tatggaagcc tgtcttcacc cagaaaggat ctgtagagaa    240
ttaaaaaatc attttccga agaatctagg aaattagaaa ataaattaag gagtatttta    300
aaacccacat attatgaatg caaagatcta ggacaaaagt gcaactctgg attttatttt    360
gatggagata tagaagctca atgcaatcat ttcaaaaaaa gatgtcaaga taaacaagag    420
agactaaaat taattaatca tattgttgat tcatctgctc tttatctcgc aaatgaagta    480
caatgcagaa cttatttcga cagttttgt ggtgcgaatg taaaacaaga attcaaacaa    540
atatgcaaca aaggagctaa tggcatatgc cctgatataa tagatgattc taaagaacat    600
tgtgctcatt tgattaatca tttaacatct cttggaattt catcgtcttc tgcttcactt    660
ccattggact attgcgactc agcgattaat tactgtaatt ctctttcgaa gttttgcacg    720
gaatcaaaac gacagtgcga ttctgttatt tctttctgca ctagcgaatc aaaaaaaact    780
gatgaatatg gttcttttat tgaccaatat cccgcggctg cagcaaatgc aaccaaatgc    840
aaggtaactt tgaaagagtt atgccaagat tcaagcaaaa aagactctta ttcaacacta    900
tgtgcttata taaagatgg ttataccgaa atatgtaaaa acttaagaaa ttcatagaa    960 aaagcatgcg agaatttgag aattcattta catacttatg atacaaactc actcaatacg   1020
aataaaggat ctgctcaaga tagatgcact tatataagaa atctttactt taaatttaaa   1080
aatatatgtt tattggttga tccttttctat gacttatctc ctattatcac tcaagaatgt   1140
aaaaccaata tatccgaacc agcactgcct gataaggatc ctcaacctac atcttcacct   1200
cagccaaaac ctcggccaag acctcgacct caacctcaac ctcatccaca tccaaaacct   1260
cagcctcagc cgacgccaga acctcagcct cagccggcgc cagaacctcg acctcagccg   1320
acgtcaaaac ctcgacctca gccaacgtca aaacctcgac ctcagccgac gccagaacct   1380
cgacctctgc cggtgccagg acctggacct ctgccggtgc caggacctcg acctcaacct   1440
cggtgccagg cctcgacctc gcctcaacct caacctcagc ctcaacctca acctcagcct   1500
cagcctcagc ctcagcctca gcctcaacct cagccgaagc ctcaaccacc atctcagtca   1560
acatcagaat cagcatcgca atccaaaacca aaaccaacaa cacaaacaaa accgtcaccg   1620
agaccacacc caaagccggt gccaaaacca tcatcgatag acacaggacc atcaaaatcg   1680
```

-continued

```
gattcaagct tcatttttac agtaacaaaa acaataacaa agatatcaga aacagaaaaa      1740
ccatctacaa aaccatctgt gaaaccaacc tctacaaaga caacatcaaa accatctaca      1800
aaaccatcta caaaccatc tgtaaaacca gcctctacaa agacaacatc agaatcagaa       1860
aaaccaacat tggaagaagt tccagaaact aaagggaatg gtgtaagagt aataggattt      1920
gaggggttac aattattatc aatgattgtt gcaataataa ttgggatatg gataatgtaa      1980
```

<210> SEQ ID NO 67
<211> LENGTH: 659
<212> TYPE: PRT
<213> ORGANISM: Artificial Sequence
<220> FEATURE:
<223> OTHER INFORMATION: Description of Artificial Sequence:  deduced
      partial amino acid sequence of P. carinii cDNA
      clone A12

<400> SEQUENCE: 67

```
Leu Asp Thr Arg Ala Asn Val Phe Ser Ser Cys Tyr Lys Glu Asp Met
  1               5                  10                  15

Asp Phe Ser Ala Lys Leu Asp Leu Leu Asn Arg Ile Lys Asp Lys Ile
             20                  25                  30

Val Val Pro Lys Gly Asn Thr Arg Tyr Phe Val Glu Leu Leu Cys Lys
         35                  40                  45

Ser Tyr Ile Val Ala Glu Cys Ser Ala Ser Asp Leu Met Phe Lys Ser
     50                  55                  60

Tyr Ala Leu Met Glu Ala Cys Leu His Pro Glu Arg Ile Cys Arg Glu
 65                  70                  75                  80

Leu Lys Asn His Phe Ser Glu Glu Ser Arg Lys Leu Glu Asn Lys Leu
                 85                  90                  95

Arg Ser Ile Leu Lys Pro Thr Tyr Tyr Glu Cys Lys Asp Leu Gly Gln
            100                 105                 110

Lys Cys Asn Ser Gly Phe Tyr Phe Asp Gly Asp Ile Glu Ala Gln Cys
        115                 120                 125

Asn His Phe Lys Lys Arg Cys Gln Asp Lys Gln Glu Arg Leu Lys Leu
    130                 135                 140

Ile Asn His Ile Val Asp Ser Ser Ala Leu Tyr Leu Ala Asn Glu Val
145                 150                 155                 160

Gln Cys Arg Thr Tyr Phe Asp Ser Phe Cys Gly Ala Asn Val Lys Gln
                165                 170                 175

Glu Phe Lys Gln Ile Cys Asn Lys Gly Ala Asn Gly Ile Cys Pro Asp
            180                 185                 190

Ile Ile Asp Asp Ser Lys Glu His Cys Ala His Leu Ile Asn His Leu
        195                 200                 205

Thr Ser Leu Gly Ile Ser Ser Ser Ala Ser Leu Pro Leu Asp Tyr
    210                 215                 220

Cys Asp Ser Ala Ile Asn Tyr Cys Asn Ser Leu Ser Lys Phe Cys Thr
225                 230                 235                 240

Glu Ser Lys Arg Gln Cys Asp Ser Val Ile Ser Phe Cys Thr Ser Glu
                245                 250                 255

Ser Lys Lys Thr Asp Glu Tyr Gly Ser Phe Ile Asp Gln Tyr Pro Ala
            260                 265                 270

Ala Ala Ala Asn Ala Thr Lys Cys Lys Val Thr Leu Lys Glu Leu Cys
        275                 280                 285

Gln Asp Ser Ser Lys Lys Asp Ser Tyr Ser Thr Leu Cys Ala Tyr Asn
    290                 295                 300
```

```
-continued

Lys Asp Gly Tyr Thr Glu Ile Cys Lys Asn Leu Arg Asn Phe Ile Glu
305                 310                 315                 320

Lys Ala Cys Glu Asn Leu Arg Ile His Leu His Thr Tyr Asp Thr Asn
                325                 330                 335

Ser Leu Asn Thr Asn Lys Gly Ser Ala Gln Asp Arg Cys Thr Tyr Ile
                340                 345                 350

Arg Asn Leu Tyr Phe Lys Phe Lys Asn Ile Cys Leu Leu Val Asp Pro
                355                 360                 365

Phe Tyr Asp Leu Ser Pro Ile Ile Thr Gln Glu Cys Lys Thr Asn Ile
            370                 375                 380

Ser Glu Pro Ala Leu Pro Asp Lys Asp Pro Gln Pro Thr Ser Ser Pro
385                 390                 395                 400

Gln Pro Lys Pro Arg Pro Arg Pro Arg Pro Gln Pro Gln Pro His Pro
                405                 410                 415

His Pro Lys Pro Gln Pro Gln Pro Thr Pro Glu Pro Gln Pro Gln Pro
                420                 425                 430

Ala Pro Glu Pro Arg Pro Gln Pro Thr Ser Lys Pro Arg Pro Gln Pro
                435                 440                 445

Thr Ser Lys Pro Arg Pro Gln Pro Thr Pro Glu Pro Arg Pro Leu Pro
450                 455                 460

Val Pro Gly Pro Gly Pro Leu Pro Val Pro Gly Pro Arg Pro Gln Pro
465                 470                 475                 480

Gln Pro Gln Pro Gln Pro Gln Pro Gln Pro Gln Pro Gln Pro Gln Pro
                485                 490                 495

Gln Pro Gln Pro Gln Pro Gln Pro Gln Pro Gln Pro Gln Pro Gln Pro
                500                 505                 510

Lys Pro Gln Pro Pro Ser Gln Ser Thr Ser Glu Ser Ala Ser Gln Ser
                515                 520                 525

Lys Pro Lys Pro Thr Thr Gln Thr Lys Pro Ser Pro Arg Pro His Pro
                530                 535                 540

Lys Pro Val Pro Lys Pro Ser Ser Ile Asp Thr Gly Pro Ser Lys Ser
545                 550                 555                 560

Asp Ser Ser Phe Ile Phe Thr Val Thr Lys Thr Ile Thr Lys Ile Ser
                565                 570                 575

Glu Thr Glu Lys Pro Ser Thr Lys Pro Ser Val Lys Pro Thr Ser Thr
                580                 585                 590

Lys Thr Thr Ser Lys Pro Ser Thr Lys Pro Ser Thr Lys Pro Ser Val
            595                 600                 605

Lys Pro Ala Ser Thr Lys Thr Thr Ser Glu Ser Glu Lys Pro Thr Leu
610                 615                 620

Glu Glu Val Pro Glu Thr Lys Gly Asn Gly Val Arg Val Ile Gly Phe
625                 630                 635                 640

Glu Gly Leu Gln Leu Leu Ser Met Ile Val Ala Ile Ile Ile Gly Ile
                645                 650                 655

Trp Ile Met
```

POLYPEPTIDES AND IMMUNOGENIC CONJUGATES CAPABLE OF INDUCING ANTIBODIES AGAINST PATHOGENS, AND USES THEREOF

This application is a national stage application under 35 U.S.C. §371 from PCT Application No. PCT/US2004/043959, filed Dec. 31, 2004, which claims the benefit of U.S. Provisional Patent Application Ser. No. 60/533,788, filed Dec. 31, 2003, which is hereby incorporated by reference in its entirety.

The present invention was made, at least in part, with funding received from the National Institutes of Heath under grant numbers AI23302, AI45479, and 5T32AI07362 (NI-AID). The U.S. government may have certain rights in this invention.

FIELD OF THE INVENTION

The present invention relates to novel polypeptides and immunogenic conjugates which are capable of inducing antibodies against pathogens, as well as use of the peptides, immunogenic conjugates, or antibodies to provide active or passive immunity against pathogens.

BACKGROUND OF THE INVENTION

*Pneumocystis carinii* is an opportunistic fungal pathogen that causes pneumonia (*P. carinii* pneumonia; PCP) in the immunocompromised host. PCP, as well as other opportunistic infections, underwent a dramatic rise in prevalence with the onset of the AIDS epidemic (Morris et al., "Update on the Epidemiology and Transmission of *Pneumocystis carinii*," *Microbes Infect.* 4:95-103 (2002)). With the development of highly effective anti-retroviral therapy, the prevalence of PCP in AIDS patients has declined, though it remains the most commonly diagnosed serious opportunistic infection in AIDS patients (Stringer et al., "Molecular Biology and Epidemiology of *Pneumocystis carinii* Infection in AIDS," *Aids* 10:561-571 (1996)). PCP is also prevalent in persons undergoing chemotherapy or other immunosuppressive therapy for cancer and organ transplantations (Morris et al., "Update on the Epidemiology and Transmission of *Pneumocystis carinii*," *Microbes Infect.* 4:95-103 (2002)). The most common drug treatments for *P. carinii* infections are trimethoprim-sulfamethoxazole and aerosolized pentamidine. Because adverse side effects, recurrent infections, and poor compliance are problems with these drugs, alternative treatments or preventative measures against PCP are needed to eradicate this serious opportunistic infection.

*P. carinii* cannot be continuously cultured outside of its host. *P. carinii* also has a host species-dependent specificity which complicates the ability to use animal derived organisms to immunize humans. *P. carinii* organisms derived from different hosts have isoform variants of common antigens resulting in different (i.e., non-crossreactive) antigenic determinants (Gigliotti et al., "Antigenic Characterization of *Pneumocystis carinii*," *Semin. Respir. Infect.* 13:313-322 (1998); Gigliotti et al., "Further Evidence of Host Species-Specific Variation in Antigens of *Pneumocystis carinii* Using the Polymerase Chain Reaction," *J. Infect. Dis.* 168:191-194 (1993)). Attempts to infect laboratory animals with *P. carinii* isolated from heterologous mammalian species have met with little to no success (Aliouat et al., "*Pneumocystis* Cross Infection Experiments Using SCID Mice and Nude Rats as Recipient Host, Showed Strong Host-Species Specificity," *J. Eukaryot. Microbiol.* 41:71S (1994); Atzori et al., "*P. carinii* Host Specificity: Attempt of Cross Infections With Human Derived Strains in Rats," *J. Eukaryot. Microbiol.* 46:112S (1999); Gigliotti et al., "*Pneumocystis carinii* Host Origin Defines the Antibody Specificity and Protective Response Induced by Immunization," *J. Infect. Dis.* 176:1322-1326 (1997)). However, immunocompetent mice immunized with whole mouse *P. carinii* are protected from developing PCP after T cell depletion and subsequent challenge, whereas unimmunized cohorts are not protected (Harmsen et al., "Active Immunity to *Pneumocystis carinii* Reinfection in T-cell-depleted Mice," *Infect. Immun.* 63:2391-2395 (1995)).

The surface glycoprotein gpA is an abundant and immunodominant antigen of *P. carinii* (Graves et al., "Development and Characterization of Monoclonal Antibodies to *Pneumocystis carinii*," *Infect. Immun.* 51:125-133 (1986)), although immunization with this antigen does not adequately protect against infection in a mouse model of PCP (Gigliotti et al., "Immunization with *Pneumocystis carinii* gpA is Immunogenic But Not Protective in a Mouse Model of *P. carinii* Pneumonia," *Infect. Immun.* 66:3179-3182 (1998)). The majority of monoclonal antibodies (mAb) against *P. carinii* surface antigens react with only isoforms showing host species-specificity identical to that of the immunogen (Gigliotti et al., "*Pneumocystis carinii* Host Origin Defines the Antibody Specificity and Protective Response Induced by Immunization," *J. Infect. Dis.* 176:1322-1326 (1997)). MAb 4F11 was obtained by selective screening of anti-mouse *P. carinii* hybridomas for recognition of *P. carinii* antigens other than gpA (Lee et al., "Molecular Characterization of KEX1, a Kexin-Like Protease in Mouse *Pneumocystis carinii*," *Gene* 242:141-150 (2000)). MAb 4F11 confers passive prophylaxis against development of PCP when administered intranasally to SCID mice (Gigliotti et al., "Passive Intranasal Monoclonal Antibody Prophylaxis Against Murine *Pneumocystis carinii* Pneumonia," *Infect. Immun.* 70:1069-1074 (2002)). Furthermore, mAb 4F11 recognizes surface antigens of *P. carinii* derived from different hosts, including humans. A screen of a *P. carinii* cDNA expression library using mAb 4F11 revealed a number of positive clones, including mouse *P. carinii* Kex1 (Lee et al., "Molecular Characterization of KEX1, a Kexin-Like Protease in Mouse *Pneumocystis carinii*," *Gene* 242:141-150 (2000)). Based on sequence homology to its ortholog in *Saccharomyces cerevisiae*, Kex1 is a member of the kexin family of subtilisin-like proteases (Lee et al., "Molecular Characterization of KEX1, a Kexin-Like Protease in Mouse *Pneumocystis carinii*," *Gene* 242:141-150 (2000)).

It would be desirable to identify a linear or conformational epitope that is recognized by mAb 4F11, which would then allow the development of passive and active vaccines for treating or preventing *Pneumocystis* infection.

The present invention is directed to overcoming these and other deficiencies in the art.

SUMMARY OF THE INVENTION

A first aspect of the present invention relates to an isolated protein or polypeptide that includes the amino acid sequence

X-P-X-P-X-X-P-X-P        (SEQ ID NO: 1)

wherein
  X at position 1 is R, K, or Q;
  X at position 3 is any amino acid;
  X at position 5 is optional and can be P;
  X at position 6 is K, Q, or R; and
  X at position 8 is any amino acid; and wherein the isolated protein or polypeptide is not a full-length protein whose sequence had been reported in GenBank prior to Dec. 31, 2003, such as a full-length *Pneumocystis* kexin or a full-length *Streptococcus pneumoniae* pneumococcal surface protein A (PspA). Pharmaceutical compositions containing the isolated protein or polypeptide are also disclosed.

A second aspect of the present invention relates to an immunogenic conjugate that includes the isolated protein or polypeptide according to the first aspect of the present invention, which protein or polypeptide is covalently or non-covalently bonded to a carrier molecule. Pharmaceutical compositions containing the immunogenic conjugate are also disclosed.

A third aspect of the present invention relates to an antibody raised against either the isolated protein or polypeptide according to the first aspect of the present invention or the immunogenic conjugate according to the second aspect of the present invention. The antibody is not mAb 4F11, mAb 4F11 (G1), or mAb 1G4 (Gigliotti et al., "Passive Intranasal Monoclonal Antibody Prophylaxis Against Murine *Pneumocystis carinii* Pneumonia," *Infect. Immun.* 70:1069-1074 (2002), which is hereby incorporated by reference in its entirety). Antisera and pharmaceutical compositions containing the antibody are also disclosed. A diagnostic kit containing one or more of the antibodies is further disclosed.

A fourth aspect of the present invention relates to an immunogenic conjugate that includes a carrier protein or polypeptide comprising the amino acid sequence

```
    X-P-X-P-X-X-P-X-P        (SEQ ID NO: 1)
``` wherein
X at position 1 is R, K, or Q;
X at position 3 is any amino acid;
X at position 5 is optional and can be P;
X at position 6 is K, Q, or R; and
X at position 8 is any amino acid; and a bacterial molecule covalently or non-covalently bonded to the carrier protein or polypeptide. Pharmaceutical compositions containing the immunogenic conjugate are also disclosed.

A fifth aspect of the present invention relates to an antibody raised against the immunogenic conjugate according to the fourth aspect of the present invention. The antibody is not mAb 4F11, mAb 4F11(G1), or mAb 1G4 (Gigliotti et al., "Passive Intranasal Monoclonal Antibody Prophylaxis Against Murine *Pneumocystis carinii* Pneumonia," *Infect. Immun.* 70:1069-1074 (2002), which is hereby incorporated by reference in its entirety). Antisera and pharmaceutical compositions containing the antibody are also disclosed. A diagnostic kit containing the antibody is further disclosed.

A sixth aspect of the present invention relates to a method of treating or preventing infection in a patient by a *Pneumocystis* organism This method of the invention includes: administering to a patient an amount of one or more agents selected from the group of (i) the protein or polypeptide according to the first aspect of the present invention, (ii) an immunogenic conjugate according to the second aspect of the present invention (which includes the protein or polypeptide of (i) covalently or non-covalently bonded to a carrier molecule), (iii) an immunogenic conjugate according to the fourth aspect of the present invention (which includes a carrier protein or polypeptide containing the protein or polypeptide of (i) and a bacterial molecule covalently or non-covalently bonded to the carrier protein or polypeptide), or (iv) combinations thereof, where the amount is effective to induce an immune response in the patient and thereby treat or prevent infection of the patient by a *Pneumocystis* organism.

A seventh aspect of the present invention relates to a method of treating or preventing infection in a patient by a *Pneumocystis* organism. This method of the invention includes: administering to a patient an amount of either (i) an antibody according to the third aspect of the present invention, (ii) an antibody according to the fifth aspect of the present invention, (iii) an antibody that recognizes *Pneumocystis* kexin and the protein of clone A12, or (iv) any combination thereof, wherein the amount of the one or more antibodies is effective to treat or prevent infection by a *Pneumocystis* organism.

An eighth aspect of the present invention relates to a method of treating or preventing infection in a patient by a *Pneumocystis* organism. This method of the invention includes: administering to a patient an amount of a *Pneumocystis* protein or polypeptide comprising the amino acid sequence of clone A12, a *Pneumocystis* kexin, or any combination thereof, where the amount is effective to induce an immune response in the patient and thereby treat or prevent infection of the patient by the *Pneumocystis* organism.

A ninth aspect of the present invention relates to a diagnostic kit that includes: either (i) an antibody according to the third aspect of the present invention, (ii) an antibody according to the fifth aspect of the present invention, or both.

A tenth aspect of the present invention relates to an isolated nucleic acid molecule encoding the isolated protein or polypeptide according to the first aspect of the present invention, which nucleic acid molecule can be either DNA or RNA. DNA constructs, expression vectors, host cells, and liposomal or polymeric delivery vehicles containing the nucleic acid (DNA) molecule are also disclosed.

Having identified and described another mouse *P. carinii* antigen (encoded by cDNA clone A12) that is recognized by mAb 4F11, and having mapped epitopes recognized by mAb 4F11 within both mouse *P. carinii* Kex1 and cDNA clone A12, the present invention relates to the use of polypeptides containing the epitope to afford passive and active immunization strategies.

Quite surprisingly, however, demonstrated hereinafter is the fact that a *Streptococcus pneumoniae* cell surface antigen, PspA, shares this same epitope that is recognized by mAb 4F11. Thus, administration of agents containing the shared epitope or recognizing said epitope will be useful for protecting against or treating both *Pneumocystis* and *Streptococcus pneumoniae* infection. As demonstrated herein, mab 4F11 (raised against *Pneumocystis* kexin) not only provides protection against a challenge from *P. carinii*, but may also be protective against a challenge from *S. pneumoniae*. Thus, further aspects of the present invention relate to the use of *S. pneumoniae* PspA or fragments thereof to induce active protection against a *Pneumocystis* pathogen; the use of antibodies raised against *S. pneumoniae* PspA to afford passive immunity against a *Pneumocystis* pathogen; the use of a *Pneumocystis* kexin, a *Pneumocystis* protein or polypeptide comprising the amino acid sequence of clone A12, or both to induce active protection against a *Streptococcus pneumonia*; or the use an antibody raised against a *Pneumocystis* kexin or a *Pneumocystis* protein or polypeptide having the amino acid sequence of clone A12, or an antibody according to the third and fifth aspects of the present invention to afford passive immunity against *Streptococcus pneumoniae*.

BRIEF DESCRIPTION OF THE DRAWINGS

FIG. 1 shows that MAb 4F11 recognizes *P. carinii* derived from multiple different host species. MAb 4F11 and 1C7, both IgM isotypes derived against *P. carinii* in mice, were used as probes in an immunofluorescence assay of *P. carinii* isolates from mice, rats, ferrets, macaques, and humans. Each mAb was used at a concentration of approximately 50 ng/ml.

FIGS. 2A-B show the nucleotide and deduced amino acid sequence of the proline rich domains of two *P. carinii* antigens. FIG. 2A shows the nucleotide (SEQ ID NO: 2) and deduced amino acid (SEQ ID NO: 3) sequence of the proline rich domain of mouse *P. carinii* kexin showing the mAb 4F11 epitope (underline) mapped in this study. The full length sequence of the mouse *P. carinii* kexin is provided at GenBank Accession AF093132, which is hereby incorporated by reference in its entirety. FIG. 2B shows the nucleotide (SEQ ID NO: 4) and deduced amino acid (SEQ ID NO: 5) sequence of *P. carinii* cDNA clone A12, which corresponds to GenBank Accession AY371664, which is hereby incorporated by reference in its entirety.

FIGS. 5A-F show the analysis of purified recombinant epitope-thioredoxin fusion proteins. FIG. 5A is a gel stained with Coomassie Blue. FIG. 5B is a Western blot using mAb 4F11(G$_1$). FIG. 5C is a Western blot using anti-V5 epitope tag mAb. FIG. 5D is an ELISA of epitope-thioredoxin fusion constructs using mAb 4F11(G$_1$). Results are plotted as the mean±standard error of triplicate experiments. FIG. 5E shows the results of an ELISA of synthetic *P. carinii* peptides using mAb 4F11(G$_1$). Results are plotted as the mean±standard deviation of triplicate experiments. FIG. 5F shows the results of a competitive ELISA using 3-fold dilutions of synthetic *P. carinii* peptides as soluble competitors for 4F11(G1) (diluted 1:3200) binding against plate-bound sonicated mouse *P. carinii*. Results are plotted as the mean±standard deviation of triplicate experiments. The dashed line indicates the mean absorbance at 655 nm with no inhibitor and a 4F11(G1) dilution of 1:3200.

FIG. 6 shows a comparison of *P. carinii* Kex1 epitopes with *S. pneumoniae* PspA. Computer-assisted alignment of Kexin$_{856-872}$ and Kexin$_{777-787}$ (both from SEQ ID NO: 3) to *S. pneumoniae* URSP2 PspA partial deduced amino acid sequence (SEQ ID NO: 6) (GenBank Accession AY371665, which is hereby incorporated by reference in its entirety).

Figures 3, 4:
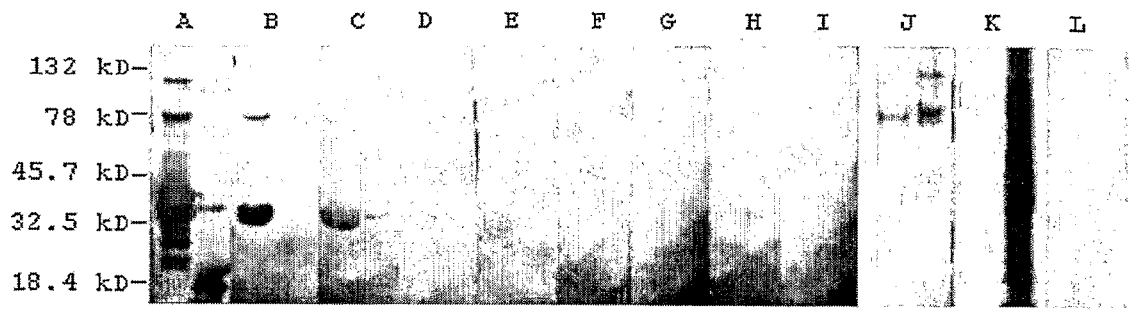
FIG. 3 is an image of Western blots prepared using *P. carinii* antigens. Each of panels A-I shows Western blots of A12$_{1-82}$ (left lane) and the thioredoxin fusion partner alone (right lane) using either (A) anti-V5 epitope tag mAb, (B) 4F11(G$_1$), (C) anti-*P. carinii* hyperimmune mouse sera 1:250 dilution, (D) anti-P.c. HIS 1:500 dilution, (E) anti-P.c. HIS 1:1000 dilution, (F) non-immunized mouse sera 1:250 dilution, (G) non-immunized mouse sera 1:500 dilution, (H) non-immunized mouse sera 1:1000 dilution, (I) irrelevant anti-*P. carinii* mab 5E12. Pooled normal mouse sera did not react with either affinity-purified antigens or total *P. carinii*-infected mouse lung homogenates. Each of panels J-L shows Western blots of mab 4F11 Reactagel column affinity purified *P. carinii* antigen (left lane) and *P. carinii*-infected mouse lung homogenate (right lane) using either (J) mab 4F11, (K) anti-Pc, HIS 1:250 dilution, or (L) anti-*H. influenzae* mab.
FIG. 4 is an alignment of amino acid sequences of inserts used in epitope analysis based on the positions of conserved proline residues. The residues of SEQ ID NOS: 3 (kexin) and 5 (clone A12) are shown.

Alignments with greater than 80% similarity with no more than one gap are shown (|=identity, :=similarity, .=gap). The clade-defining region of URSP2 PspA is underlined. The *S. pneumoniae* sequence is numbered based on the full length PspA sequence from strain BG8743 (GenBank Accession AF071803; Hollingshead et al., "Diversity of PspA: Mosaic Genes and Evidence for Past Recombination in *Streptococcus pneumoniae*," Infect. Immun. 68:5889-5900 (2000), each of which is hereby incorporated by reference in its entirety).

FIGS. 7A-D show that MAb 4F11 recognizes surface antigen PspA of *S. pneumoniae* strain URSP2. In FIG. 7A, the upper panel shows the result of *S. pneumoniae* probed with mAb 4F11 and FITC-conjugated secondary antibody; the right panel is an enlargement of boxed area showing mAb 4F11 staining of *S. pneunoniae* diplococcus. In the lower panel, *S. pneumoniae* was probed with isotype matched mAb 2B5 and FITC-conjugated secondary antibody. FIG. 7B is a Western blot of *P. carinii*-infected mouse lung homogenates (lane 2) and *S. pneumoniae* URSP2 culture lysates (lane 3) probed with mAb 4F11. Lane 1 contains molecular weight markers. FIGS. 7C-D are Western blots probed with either (7C) mAb 4F11(G$_1$) or (7D) anti-V5 epitope tag mAb. In each of these figures, lane 1 contains purified recombinant URSP2 PspA: thioredoxin fusion protein, lane 2 contains thioredoxin only, and lane 3 contains molecular weight markers.

FIGS. 8A-B show a more complete fragment of the nucleotide sequence (SEQ ID NO: 66) corresponding to clone A12 and the putative amino acid sequence (SEQ ID NO: 67) of the encoded polypeptide. The portion of the amino acid sequence and nucleotide sequence that were obtained subsequent to reporting the sequence of clone A12 (as in FIG. 2B) are identified by italics.

DETAILED DESCRIPTION OF THE INVENTION

The present invention relates to the identification of an epitope shared by several *Pneumocystis* proteins, including *Pneumocystis* Kex1 (a kexin) and the *Pneumocystis* protein encoded by clone A12 (identified herein), as well as *Streptococcus pneumoniae* pneumococcal surface protein A (PspA). Having identified an epitope shared by *Pneumocystis* Kex1 and *Streptococcus pneumoniae* PspA, the present invention further relates to various active agents that can be used to provide passive or active immunity to *Pneumocystis* and, possibly, *Streptococcus pneumoniae*. Such active agents include, without limitation: isolated proteins or polypeptides that contain the shared epitope; immunogenic conjugates that include as a component thereof, a protein or polypeptide that contains the shared epitope; antibodies that are raised against the shared epitope and recognize the same; and nucleic acid vectors that encodes proteins (whether a fusion protein or otherwise) that contain the shared epitope.

A first type of active agent of the present invention is an isolated protein or polypeptide that contains the amino acid sequence:

X-P-X-P-X-X-P-X-P        (SEQ ID NO: 1)

wherein

X at position 1 is R, K, or Q;

X at position 3 is any amino acid;

X at position 5 is optional and can be P;

X at position 6 is K, Q, or R; and

X at position 8 is any amino acid.

The isolated protein or polypeptide can be any polypeptide that contains the above amino acid sequence of SEQ ID NO: 1, as long as the protein or polypeptide is not a full-length protein whose sequence had been reported in GenBank prior to Dec. 31, 2003, such as the full-length *Pneumocystis* Kex1 or a full-length *Streptococcus pneumoniae* PspA. Full-length proteins reported in GenBank prior to the filing date of the present application can be identified by performing a BLAST search using any of SEQ ID NOS: 1 and 7-24 (infra).

Exemplary proteins or polypeptides are those that contain any one of the following amino acid sequences (where X is any amino acid):

| | |
|---|---|
| R-P-X-P-P-K-P-X-P, | (SEQ ID NO: 7) |
| R-P-X-P-P-Q-P-X-P, | (SEQ ID NO: 8) |
| R-P-X-P-P-R-P-X-P, | (SEQ ID NO: 9) |
| K-P-X-P-P-K-P-X-P, | (SEQ ID NO: 10) |
| K-P-X-P-P-Q-P-X-P, | (SEQ ID NO: 11) |
| K-P-X-P-P-R-P-X-P, | (SEQ ID NO: 12) |
| Q-P-X-P-P-K-P-X-P, | (SEQ ID NO: 13) |
| Q-P-X-P-P-Q-P-X-P, | (SEQ ID NO: 14) |
| Q-P-X-P-P-R-P-X-P, | (SEQ ID NO: 15) |
| R-P-X-P-K-P-X-P, | (SEQ ID NO: 16) |
| R-P-X-P-Q-P-X-P, | (SEQ ID NO: 17) |
| R-P-X-P-R-P-X-P, | (SEQ ID NO: 18) |
| K-P-X-P-K-P-X-P, | (SEQ ID NO: 19) |
| K-P-X-P-Q-P-X-P, | (SEQ ID NO: 20) |
| K-P-X-P-R-P-X-P, | (SEQ ID NO: 21) |
| Q-P-X-P-K-P-X-P, | (SEQ ID NO: 22) |
| Q-P-X-P-Q-P-X-P, and | (SEQ ID NO: 23) |
| Q-P-X-P-R-P-X-P. | (SEQ ID NO: 24) |

The isolated protein or polypeptide can also contain one or more repeats of SEQ ID NO: 1, where each of the repeats is the same or different (but still matching the consensus). The repeats can either be consecutive, for example (X-P-X-P-X-X-P-X-P)$_n$ where n is a whole number greater than 1; or periodic, for example $X_q$-[$X_p$-(X-P-X-P-X-X-P-X-P)]$_n$-$X_q$ where $X_p$ can be one or more amino acids and the same or different in each repeat, each $X_q$ is optional or can be one or more amino acids, and n is a whole number greater than 1.

Isolated polypeptides or proteins in accordance with this aspect of the present invention can be fragments of previously identified proteins (that contain the amino acid sequence of SEQ ID NO: 1), including any such protein that had been reported in GenBank prior to the filing date of the present application (as identified by performing a BLAST search using any of SEQ ID NOS: 1-24). Such fragments can contain 600 amino acids or less, preferably 500 amino acids or less, 400 amino acids or less, 300 amino acids or less, or 200 amino acids or less. More preferably, the fragments of previously identified proteins contain 100 amino acids or less, 50 amino acids or less, or 25 amino acids or less.

One embodiment of the isolated protein or polypeptide contains an amino acid sequence according to SEQ ID NO: 1 and is a fragment of a *Pneumocystis* kexin, preferably a kexin from *P. carinii* that is pathogenic to mammalian hosts such as human, mouse, rat, etc. The amino acid and nucleotide sequences of *P. carinii* kexins have been reported at GenBank accessions AF093132 (mouse host), U62910 (rat host), each of which is hereby incorporated by reference in its entirety.

Another embodiment of the isolated protein or polypeptide contains an amino acid sequence according to SEQ ID NO: 1 and is a fragment of *Streptococcus pneumoniae* PspA. The amino acid and nucleotide sequences of *Streptococcus pneumoniae* PspA from various strains have been reported at GenBank, only several of which include accessions AE008396 and AAK98925 (strain R6); U89711 and AAC62252 (strain Rx1); and M74122 and AAA27018, each of which is hereby incorporated by reference in its entirety.

Isolated polypeptides or proteins in accordance with another aspect of the present invention can be either full length or fragments of newly identified proteins.

According to another embodiment, the isolated protein or polypeptide contains an amino acid sequence according to SEQ ID NO: 1 and is either a fragment of SEQ ID NO: 5 or the full length protein that contains SEQ ID NO: 5 (see FIG. 2B) or SEQ ID NO: 67 (see FIGS. 8A-B).

Variants of the isolated protein or polypeptide of this embodiment are encoded by a nucleic acid molecule that (i) contains the nucleotide sequence of 1-837 of the *Pneumocystis* A12 clone (SEQ ID NO: 4, see FIG. 2B) or the nucleotide sequence of SEQ ID NO: 66 (see FIGS. 8A-B), (ii) shares at least about 85 percent identity, more preferably at least about 90 or at least about 95 percent identity, to the nucleotide sequence of 1-837 of the *Pneumocystis* A12 clone (SEQ ID NO: 4) or the nucleotide sequence of SEQ ID NO: 66, or (iii) hybridizes overnight (i.e., about 12 to about 18 hours) to the nucleotide sequence of 1-837 of the *Pneumocystis* A12 clone (SEQ ID NO: 4) or the nucleotide sequence of SEQ ID NO: 66 under stringency conditions of a hybridization medium that contains at most about 10× standard sodium citrate ("SSC") and a temperature of about 50° C. or greater followed by wash conditions at or above stringency conditions of the hybridization (e.g., 0.1×SSC at 60° C.). The *Pneumocystis* A12 clone is described in the accompanying Examples and at GenBank accession AY371664, which is hereby incorporated by reference in its entirety.

Isolated nucleic acid molecules that encode the isolated proteins or polypeptides of the present invention are also contemplated. Such nucleic acid molecules can be either DNA or RNA. Various embodiments of the isolated nucleic acid molecule include, without limitation, those nucleic acid molecules encoding a fragment of a *Pneumocystis* kexin, a fragment of *Streptococcus pneumoniae* protein A, or the protein or polypeptide that includes the amino acid sequence of *Pneumocystis carinii* clone A12 (SEQ ID NO: 4) as described above. The DNA molecules of the present invention can be in isolated form or present as a component in a DNA construct or expression vector that is useful for expressing the isolated proteins or polypeptides. This aspect is described in greater detail hereinafter.

A second type of active agent contains the isolated protein(s) or polypeptide(s) as a component of an immunogenic conjugate, which conjugate can induce the production of antibodies against the above-identified epitopes.

According to one embodiment, the immunogenic conjugate includes a carrier molecule to which the protein or polypeptide is covalently or non-covalently bonded. Exemplary carrier molecules include, without limitation, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein. Each of these carrier molecules are safe for administration and immunologically effective; they are non-toxic and the incidence of allergic reaction is well known for each of them.

The immunogenic conjugate can further include a bacterial molecule covalently or non-covalently bonded to either the carrier molecule or the isolated protein or polypeptide (i.e., forming a three-component conjugate). Suitable bacterial molecules include, without limitation, lipopolysaccharides, polysaccharides that are distinct of the carrier molecules described above, or proteins or polypeptides that are distinct of both the isolated protein or polypeptide and the carrier molecules described above.

When all components of the immunogenic conjugate are polypeptides, the immunogenic conjugate can take the form of a fusion or chimeric protein that includes the protein or polypeptide of the present invention coupled by an in-frame gene fusion to a carrier protein or polypeptide (as the carrier molecule). In this arrangement, the carrier protein or polypeptide can be any of the above-identified proteins or polypeptides, as well as plasmid-, chromosomal (prokaryotic or eukaryotic)- or viral-encoded carrier polypeptides or proteins.

An exemplary immunogenic conjugate of the invention includes a protein or polypeptide containing the amino acid sequence of SEQ ID NO: 1 (or any one of SEQ ID NOS: 7-24) and a bacterial molecule covalently or non-covalently bonded to the carrier protein or polypeptide. The protein or polypeptide containing the amino acid sequence of SEQ ID NO: 1 can be either a full length protein or any fragments thereof, such as by way of example, a *Pneumocystis* kexin, the *Pneumocystis* protein containing the amino acid sequence of SEQ ID NO: 5, or *Streptococcus pneumoniae* PspA. The bacterial molecule can be any of the type identified above, but preferably a pneumococcal capsular polysaccharide, one or more meningococcal outer membrane proteins, or a combination thereof.

Immunogenic conjugates that are not fusion proteins per se, i.e., contain a non-proteinaceous component, can be formed using standard conjugation conditions. For example, according to one approach conjugation can be achieved via an EDC-catalyzed amide linkage to the N-terminus of the protein or polypeptide. Alternatively, conjugation can be achieved via aminoalkylation according to the Mannich reaction. Once these conjugates have been prepared, they can be isolated and purified according to standard procedures.

Immunogenic conjugates that are fusion proteins can be formed using standard recombinant DNA techniques. Basically, DNA molecules encoding the various polypeptide components of the immunogenic conjugate (to be prepared) are ligated together along with appropriate regulatory elements that provide for expression (i.e., transcription and translation) of the fusion protein encoded by the DNA molecule. When recombinantly produced, the immunogenic fusion proteins are expressed in a recombinant host cell, typically, although not exclusively, a prokaryote.

When a prokaryotic host cell is selected for subsequent transformation, the promoter region used to construct the recombinant DNA molecule (i.e., transgene) should be appropriate for the particular host. The DNA sequences of eukaryotic promoters, as described infra for expression in eukaryotic host cells, differ from those of prokaryotic promoters. Eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon ("ATG") to provide a ribosome binding site. Thus, any SD-ATG combination that can be utilized by host cell ribosomes may be employed. Such combinations include, but are not limited to, the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Mammalian cells can also be used to recombinantly produce the immunogenic fusion proteins of the present invention. Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293

(ATCC No. 1573), CHOP, and NS-1 cells. Suitable expression vectors for directing expression in mammalian cells generally include a promoter, as well as other transcription and translation control sequences known in the art. Common promoters include SV40, MMTV, metallothionein-1, adenovirus E1a, CMV, immediate early, immunoglobulin heavy chain promoter and enhancer, and RSV-LTR.

Regardless of the selection of host cell, once the DNA molecule coding for an immunogenic fusion protein of the present invention has been ligated to its appropriate regulatory regions using well known molecular cloning techniques, it can then be introduced into a suitable vector or otherwise introduced directly into a host cell using transformation protocols well known in the art (Sambrook et al., *Molecular Cloning: A Laboratory Manual*, Second Edition, Cold Spring Harbor Press, NY (1989), which is hereby incorporated by reference in its entirety).

The recombinant molecule can be introduced into host cells via transformation, particularly transduction, conjugation, mobilization, or electroporation. Suitable host cells include, but are not limited to, bacteria, yeast, mammalian cells, insect cells, plant cells, and the like. The host cells, when grown in an appropriate medium, are capable of expressing the immunogenic fusion protein, which can then be isolated therefrom and, if necessary, purified. The immunogenic fusion protein is preferably produced in purified form (preferably at least about 60%, more preferably 80%, pure) by conventional techniques.

A third type of active agent is an antibody that can recognize (or bind to) an epitope containing SEQ ID NO: 1 (or SEQ ID NOS: 7-24), either in whole or in part. Such antibodies of the present invention can be raised against the isolated proteins or polypeptides of the present invention, or any immunogenic conjugates of the present invention, all of which include the amino acid sequence of SEQ ID NO: 1 (or SEQ ID NOS: 7-24). Thus, the antibodies will have been raised against an antigenic substance that includes the amino acid sequence of SEQ ID NO: 1 (or SEQ ID NOS: 7-24) as at least part of an epitope.

The antibodies of the present invention can be either monoclonal antibodies, polyclonal antibodies, or functional fragments or variants thereof.

Monoclonal antibody production can be effected by techniques that are well-known in the art. Basically, the process involves first obtaining immune cells (lymphocytes) from the spleen of a mammal (e.g., mouse) that has been previously immunized with the antigen of interest (the protein or polypeptide or immunogenic conjugates of the invention) either in vivo or in vitro. The antibody-secreting lymphocytes are then fused with myeloma cells or transformed cells, which are capable of replicating indefinitely in cell culture. The resulting fused cells, or hybridomas, are immortal, immunoglobulin-secreting cell lines that can be cultured in vitro. Upon culturing the hybridomas, the resulting colonies can be screened for the production of desired monoclonal antibodies. Colonies producing such antibodies are cloned and grown either in vivo or in vitro to produce large quantities of antibody. A description of the theoretical basis and practical methodology of fusing such cells is set forth in Kohler and Milstein, *Nature* 256:495 (1975), which is hereby incorporated by reference in its entirety.

Mammalian lymphocytes are immunized by in vivo immunization of the animal (e.g., a mouse, rat, rabbit, or human) with the protein or polypeptide or immunogenic conjugates of the invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol* 6:511 (1976), which is hereby incorporated by reference in its entirety). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described. Human hybridomas can be prepared using the EBV-hybridoma technique monoclonal antibodies (Cole et al., in *Monoclonal, Antibodies and Cancer Therapy*, Alan R. Liss, Inc., pp. 77-96 (1985), which is hereby incorporated by reference in its entirety). Human antibodies may be used and can be obtained by using human hybridomas (Cote et al., *Proc. Natl. Acad. Sci. USA* 80:2026-2030 (1983), which is hereby incorporated by reference in its entirety) or by transforming human B cells with EBV virus in vitro (Cole et al., in *Monoclonal Antibodies and Cancer Therapy*, Alan R. Liss, Inc., pp. 77-96 (1985), which is hereby incorporated by reference in its entirety). In addition, monoclonal antibodies can be produced in germ-free animals (see PCT/US90/02545, which is hereby incorporated by reference in its entirety).

Procedures for raising polyclonal antibodies are also well known. Typically, such antibodies can be raised by administering the antigen (the protein or polypeptide or immunogenic conjugates of the invention) subcutaneously to rabbits, mice, or rats which have first been bled to obtain pre-immune serum. The antigens can be injected as tolerated. Each injected material can contain adjuvants and the selected antigen (preferably in substantially pure or isolated form). Suitable adjuvants include, without limitation, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as bacille Calmette-Guerin and *Carynebacterium parvum*. The subject mammals are then bled one to two weeks after the first injection and periodically boosted with the same antigen (e.g., three times every six weeks). A sample of serum is then collected one to two weeks after each boost. Polyclonal antibodies can be recovered from the serum by affinity chromatography using the corresponding antigen to capture the antibody. This and other procedures for raising polyclonal antibodies are disclosed in Harlow & Lane, editors, *Antibodies: A Laboratory Manual* (1988), which is hereby incorporated by reference in its entirety.

In addition, techniques developed for the production of chimeric antibodies (Morrison et al., *Proc. Natl. Acad. Sci. USA* 81:6851-6855 (1984); Neuberger et al., *Nature* 312:604-608 (1984); Takeda et al., *Nature* 314:452-454 (1985), each of which is hereby incorporated by reference in its entirety) by splicing the genes from a mouse antibody molecule of appropriate antigen specificity together with genes from a human antibody molecule of appropriate biological activity can be used. For example, the genes from a mouse antibody molecule specific for the epitope containing the amino acid sequence of SEQ ID NO: 1 (either in whole or in part) can be spliced together with genes from a human antibody molecule of appropriate biological activity. A chimeric antibody is a molecule in which different portions are derived from different animal species, such as those having a variable region derived from a murine mAb and a human immunoglobulin constant region (e.g., U.S. Pat. No. 4,816,567 to Cabilly et al., and U.S. Pat. No. 4,816,397 to Boss et al., each of which is hereby incorporated by reference in its entirety).

In addition, techniques have been developed for the production of humanized antibodies (e.g., U.S. Pat. No. 5,585,089 to Queen, and U.S. Pat. No. 5,225,539 to Winter, each of which is hereby incorporated by reference in its entirety). An immunoglobulin light or heavy chain variable region consists of a "framework" region interrupted by three hypervariable regions, referred to as complementarity determining regions (CDRs). The extent of the framework region and CDRs have been precisely defined (see Kabat et al., "Sequences of Proteins of Immunological Interest," U.S. Department of Health and Human Services (1983), which is hereby incorporated by reference in its entirety). Briefly, humanized antibodies are antibody molecules from non-human species having one or more CDRs from the non-human species and a framework region from a human immunoglobulin molecule.

Alternatively, techniques described for the production of single chain antibodies (e.g., U.S. Pat. No. 4,946,778 to Ladner et al.; Bird, Science 242:423-426 (1988); Huston et al., Proc. Natl. Acad. Sci. USA 85:5879-5883 (1988); Ward et al., Nature 334:544-546 (1989), each of which is hereby incorporated by reference in its entirety) can be adapted to produce single chain antibodies against the epitope containing the amino acid sequence according to SEQ ID NO: 1. Single chain antibodies are formed by linking the heavy and light chain fragments of the Fv region via an amino acid bridge, resulting in a single chain polypeptide.

In addition to utilizing whole antibodies, the present invention also encompasses use of binding portions of such antibodies. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, Academic Press (New York), pp. 98-118 (1983), which is hereby incorporated by reference in its entirety. Alternatively, the Fab fragments can be generated by treating the antibody molecule with papain and a reducing agent. Alternatively, Fab expression libraries may be constructed (Huse et al., Science 246:1275-1281 (1989), which is hereby incorporated by reference in its entirety) to allow rapid and easy identification of monoclonal Fab fragments with the desired specificity.

The antibodies of the present invention may be isolated by standard techniques known in the art, such as immunoaffinity chromatography, centrifugation, precipitation, etc. The antibodies (or fragments or variants thereof) are preferably prepared in a substantially purified form (i.e., at least about 85 percent pure, more preferably 90 percent pure, even more preferably at least about 95 to 99 percent pure).

From the foregoing, it should be appreciated that the present invention also relates to the isolated immune sera containing the polyclonal antibodies, monoclonal antibodies, or fragments or variants thereof.

In addition, the antibodies generated by the vaccine formulations of the present invention can also be used in the production of anti-idiotypic antibody. The anti-idiotypic antibody can then in turn be used for immunization, in order to produce a subpopulation of antibodies that bind the initial antigen of the pathogenic microorganism, e.g., the epitope of SEQ ID NOS: 1 or 7-24 (Jerne, *Ann. Immunol.* (*Paris*) 125c: 373 (1974); Jerne et al., *EMBO J.* 1:234 (1982), each of which is hereby incorporated by reference in its entirety).

A fourth type of active agent is an expression vector encoding an immunogenic protein or polypeptide (or fusion protein) of the present invention, which expression vector can be used for in vivo expression of the protein or polypeptide in eukaryotic, preferably mammalian, organisms. Hence, this aspect relates to a DNA vaccine.

DNA inoculation represents a relatively new approach to vaccine and immune therapeutic development. The direct injection of gene expression cassettes (i.e., as plasmids) into a living host transforms a number of cells into factories for production of the introduced gene products. Expression of these delivered genes has important immunological consequences and can result in the specific immune activation of the host against the novel expressed antigens. This approach to immunization can overcome deficits of traditional antigen-based approaches and provide safe and effective prophylactic and therapeutic vaccines. The transfected host cells can express and present the antigens to the immune system (i.e., by displaying fragments of the antigens on their cell surfaces together with class I or class II major histocompatibility complexes). DNA vaccines recently have been shown to be a promising approach for immunization against a variety of infectious diseases (Michel et al., "DNA-Mediated Immunization to the Hepatitis B Surface Antigen in Mice: Aspects of the Humoral Response Mimic Hepatitis B Viral Infection in Humans," *Proc. Nat'l Acad. Sci. USA* 92:5307-5311 (1995), which is hereby incorporated by reference in its entirety). Delivery of naked DNAs containing microbial antigen genes can induce antigen-specific immune responses in the host. The induction of antigen-specific immune responses using DNA-based vaccines has shown some promising effects (Wolff et al., "Long-Term Persistence of Plasmid DNA and Foreign Gene Expression in Mouse Muscle," *Hum. Mol. Genet.* 1:363-369 (1992), which is hereby incorporated by reference in its entirety).

According to one approach, the expression vector (to be used as a DNA vaccine) is a plasmid containing a DNA construct encoding the protein or polypeptide (or fusion protein) of the present invention. The plasmid DNA can be introduced into the organism to be exposed to the DNA vaccine, preferably via intramuscular or dermal injection, which plasmid DNA can be taken up by muscle or dermal cells for expression of the protein or polypeptide.

According to another approach, the expression vector (to be used as a DNA vaccine) is an infective transformation vector, such as a viral vector.

When an infective transformation vector is employed to express a protein or polypeptide (or fusion protein) of the present invention in a host organism's cell, conventional recombinant techniques can be employed to prepare a DNA construct that encodes the protein or polypeptide and ligate the same into the infective transformation vector (Sambrook et al., *Molecular Cloning: A Laboratory Manual*, Second Edition, Cold Spring Harbor Press, NY (1989), which is hereby incorporated by reference in its entirety). The infective transformation vector so prepared can be maintained ex vivo in appropriate host cell lines, which may include bacteria, yeast, mammalian cells, insect cells, plant cells, etc. For example, having identified the protein or polypeptide to be expressed in cells of a host organism, a DNA molecule that encodes the oligoRNA can be ligated to appropriate 5' promoter regions and 3' transcription termination regions as discussed above, forming a DNA construct, so that the protein or polypeptide will be appropriately expressed in transformed cells. The selection of appropriate 5' promoters and 3' transcription termination regions is well known in the art and can be performed with routine skill. Suitable promoters for use in mammalian cells include those identified above.

Any suitable viral vector can be utilized to express the protein or polypeptide of the present invention. When transforming mammalian cells for heterologous expression of a protein or polypeptide of the present invention, exemplary viral vectors include adenovirus vectors, adeno-associated vectors, and retroviral vectors. Other suitable viral vectors now known or hereafter developed can also be utilized to deliver into cells a DNA construct encoding a protein or polypeptide of the present invention.

Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a DNA construct encoding a protein or polypeptide of the present invention. The use of adeno-associated viral gene delivery vehicles in vitro is described in Chatterjee et al., *Science* 258:1485-1488 (1992); Walsh et al., *Proc. Nat'l Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179:733-738 (1994); Miller et al., *Proc. Nat'l Acad. Sci. USA* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver into cells a DNA construct encoding a protein or polypeptide of the present invention. One such type of retroviral vector is disclosed in U.S. Pat. No. 5,849,586 to Kriegler et al., which is hereby incorporated by reference in its entirety.

Alternatively, a colloidal dispersion system can be used to deliver the DNA vaccine to the organism. Colloidal dispersion systems include macromolecule complexes, nanocapsules, microspheres, beads, and lipid-based systems including oil-in-water emulsions, micelles, mixed micelles, and liposomes. The preferred colloidal system of this invention is a lipid preparation including unilamaller and multilamellar liposomes.

Liposomes are artificial membrane vesicles that are useful as delivery vehicles in vitro and in vivo. It has been shown that large unilamellar vesicles (LUV), which range in size from about 0.2 to about 4.0 μm, can encapsulate a substantial percentage of an aqueous buffer containing DNA molecules (Fraley et al., *Trends Biochem. Sci.* 6:77 (1981), which is hereby incorporated by reference in its entirety). In addition to mammalian cells, liposomes have been used for delivery of polynucleotides in yeast and bacterial cells. For a liposome to be an efficient transfer vehicle, the following characteristics should be present: (1) encapsulation of the DNA molecules at high efficiency while not compromising their biological activity; (2) substantial binding to host organism cells; (3) delivery of the aqueous contents of the vesicle to the cell cytoplasm at high efficiency; and (4) accurate and effective expression of genetic information (Mannino et al., *Biotechniques* 6:682 (1988), which is hereby incorporated by reference in its entirety). In addition to such LUV structures, multilamellar and small unilamellar lipid preparations which incorporate various cationic lipid amphiphiles can also be mixed with anionic DNA molecules to form liposomes (Felgner et al., *Proc. Natl. Acad. Sci. USA* 84(21): 7413 (1987), which is hereby incorporated by reference in its entirety).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and typically the presence of divalent cations. The appropriate composition and preparation of cationic lipid amphiphile:DNA formulations are known to those skilled in the art, and a number of references which provide this information are available (e.g., Bennett et al., *J. Liposome Research* 6(3):545 (1996), which is hereby incorporated by reference in its entirety).

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine. Examples of cationic amphiphilic lipids useful in formulation of nucleolipid particles for polynucleotide delivery include the monovalent lipids N-[1-(2,3-dioleoyloxy)propyl]-N,N,N-trimethyl ammonium methyl-sulfate, N-[2,3-dioleoyloxy)propyl]-N,N,N-trimethyl ammonium chloride, and DC-cholesterol, the polyvalent lipids LipofectAMINE™, dioctadecylamidoglycyl spermine, Transfectam®, and other amphiphilic polyamines. These agents may be prepared with helper lipids such as dioleoyl phosphatidyl ethanolamine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization. The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

A further alternative for delivery of DNA is the use of a polymeric matrix which can provide either rapid or sustained release of the DNA vaccine to the organism. A number of polymeric matrices are known in the art and can be optimized with no more than routine skill.

Another aspect of the present invention relates to pharmaceutical compositions that contain one or more of the following active agents: (i) an antibody that recognizes an epitope containing SEQ ID NO: 1, whether the antibody has been raised against and isolated protein of the present invention or an immunogenic conjugate of the present invention; (ii) an immunogenic conjugate of the present invention; (iii) an isolated protein or polypeptide of the present invention; and (iv) a nucleic acid vector of the present invention.

The pharmaceutical compositions can include, but are not limited to, pharmaceutically suitable adjuvants, carriers, excipients, or stabilizers (collectively referred hereinafter as "carrier"). The pharmaceutical composition is preferably, though not necessarily, in liquid form such as solutions, suspensions, or emulsions. Typically, the composition will contain from about 0.01 to 99 percent, preferably from about 20 to 75 percent of one or more of the above-listed active agents, together with the adjuvants, carriers, excipients, stabilizers, etc.

The pharmaceutical compositions of the present invention can take any of a variety of known forms that are suitable for a particular mode of administration. Exemplary modes of administration include, without limitation, orally, by inhalation, by intranasal instillation, topically, transdermally, parenterally, subcutaneously, intravenous injection, intra-arterial injection, intramuscular injection, intraplurally, intraperitoneally, by intracavitary or intravesical instillation, intraocularly, intraventricularly, intralesionally, intraspinally, or by application to mucous membranes, such as, that of the nose, throat, and bronchial tubes. Of these routes, intravenous and intraarterial administration are preferred.

The pharmaceutical forms suitable for injectable use (e.g., intravenous, intra-arterial, intramuscular, etc.) include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

Oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; and sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

For use as aerosols, the active agents in solution or suspension may be packaged in a pressurized aerosol container together with suitable propellants, for example, hydrocarbon propellants like propane, butane, or isobutane with conventional adjuvants. The active agents of the present invention also may be administered in a non-pressurized form such as in a nebulizer or atomizer.

For parenteral administration, aqueous solutions in water-soluble form can be used to deliver one or more of the active agents. Additionally, suspensions of the active agent(s) may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran.

In addition to the formulations described previously, the active agent(s) may also be formulated as a depot preparation. Such long acting formulations may be administered by implantation (for example subcutaneously or intramuscularly) or by intramuscular injection. Thus, for example, the active agent(s) may be formulated with suitable polymeric or hydrophobic materials (e.g., as an emulsion in an acceptable oil) or ion exchange resins, or as sparingly soluble derivatives (e.g., as a sparingly soluble salt). Selection of polymeric matrix material is based on biocompatibility, biodegradability, mechanical properties, cosmetic appearance and interface properties. The particular application of the active agent(s) will define the appropriate formulation. Potential matrices for the compositions may be biodegradable and chemically defined calcium sulfate, tricalcium phosphate, hydroxyapatite, polylactic acid, polyglycolic acid and polyanhydrides. Other potential materials are biodegradable and biologically well-defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate, as well as other materials that are known in the drug delivery arts. The bioceramics may be altered in composition, such as in calcium-aluminate-phosphate and processing to alter pore size, particle size, particle shape, and biodegradability.

The above-identified active agents are to be administered in an amount effective to achieve their intended purpose (i.e., to induce an active immune response or provide passive immunity). While individual needs vary, determination of optimal ranges of effective amounts of each component is within the skill of the art. The quantity administered will vary depending on the patient and the mode of administration and can be any effective amount. Typical dosages include about 0.1 to about 100 mg/kg-body wt. The preferred dosages include about 1 to about 50 mg/kg-body wt. However, because patients respond differently to therapies, monitoring of the treatment efficacy should be conducted, allowing for adjustment of the dosages as needed. Treatment regimen for the administration of the above-identified active agents of the present invention can also be determined readily by those with ordinary skill in art.

By virtue of the isolated proteins or polypeptides sharing a common epitope, it is believed that the proteins or polypeptides of the present invention can be used to induce active immunity against *Pneumocystis* organisms, *Streptococcus pneumoniae*, or both. Thus, another aspect of the present invention relates to treating or prevention infection in a patient by one or both of these organisms. The treatment or prevention of infection by one or both of these organisms can be carried out by administering to the patient an amount of one or more (even two or more) active agents described above (e.g., an isolated protein or polypeptide, an immunogenic conjugate, a DNA vaccine, or pharmaceutical compositions containing the same), where the amount is effective to induce an immune response in the patient and thereby treat or prevent infection of the patient by one or both of these organisms.

The use of active immunization in the immunocompromised host would seem counter intuitive. However, the use of vaccines in immunocompromised humans has been extensively reviewed by Pirofski and Casadevall ("Use of Licensed Vaccines for Active Immunization of the Immunocompromised Host," *Clin. Microbiol. Rev.* 11(1):1-26 (1998), which is hereby incorporated by reference in its entirety). The PI of this proposal has published three clinical trials demonstrating the immunogenicity of *H. influenzae* vaccines in children with cancer and sickle cell disease (Feldman et al., "Risk of *Haemophilus influenzae* Type b Disease in Children with Cancer and Response of Immunocompromised Leukemic Children to a Conjugate Vaccine," *J. Infect. Dis.* 161(5):926-931 (1990); Shenep et al., "Response of Immunocompromised Children with Solid Tumors to a Conjugate Vaccine for *Haemophilus influenzae* Type b," *J. Pediatr.* 125(4):581-584 (1994); Gigliotti et al., "Immunization of Young Infants with Sickle Cell Disease with a *Haemophilus influenzae* Type b Saccharide-Diphtheria CRM197 Protein Conjugate Vaccine," *J. Pediatr.* 114(6):1006-10 (1989); Gigliotti et al., "Serologic Follow-up of Children With Sickle Cell Disease Immunized with a *Haemophilus influenzae* Type b Conjugate Vaccine During Early Infancy," *J. Pediatr.* 118(6):917-919 (1991), each of which is hereby incorporated by reference in its entirety). New developments in vaccine technology should enhance our ability to vaccinate at-risk hosts.

In one therapeutic embodiment, an immunogenic conjugate is utilized, which conjugate contains either a *Pneumocystis* kexin, a protein that includes the amino acid sequence of *Pneumocystis* clone A12, or fragments of either of these proteins or other polypeptides that contain the epitope of SEQ ID NO: 1 (or SEQ ID NOS: 7-24). This embodiment can be used for treating or preventing infection by, e.g., *Pneumocystis* organisms.

In another therapeutic embodiment, an immunogenic conjugate is utilized, which conjugate contains a *Streptococcus pneumoniae* PspA or a fragment thereof containing SEQ ID NO: 1 (or SEQ ID NOS: 7-24). This embodiment can be used for treating or preventing infection by, e.g., *Pneumocystis* organisms.

Another aspect of the present invention relates to a method of treating or preventing infection in a patient by a *Pneumocystis* organism that relies upon active immunity. This therapeutic embodiment involves administering to a patient an amount of a *Streptococcus pneumoniae* PspA, a *Pneumocystis* protein or polypeptide that contains the amino acid sequence of clone A12 (SEQ ID NO: 5), a *Pneumocystis* kexin (e.g., SEQ ID NO: 3), or any combination thereof, where the amount administered is effective to induce an immune response in the patient and thereby treat or prevent infection of the patient by the *Pneumocystis* organism.

In each of the embodiments that involve the induction of active immunity, immunostimulants may be co-administered to increase the immunological response. The term "immunostimulant" is intended to encompass any compound or composition which has the ability to enhance the activity of the immune system, whether it be a specific potentiating effect in combination with a specific antigen, or simply an independent effect upon the activity of one or more elements of the immune response. Immunostimulant compounds include but are not limited to mineral gels, e.g., aluminum hydroxide; surface active substances such as lysolecithin, pluronic polyols; polyanions; peptides; oil emulsions; alum, and MDP. Methods of utilizing these materials are known in the art, and it is well within the ability of the skilled artisan to determine an optimum amount of immunostimulant for a given active vaccine. More than one immunostimulant may be used in a given formulation. The immunogen may also be incorporated into liposomes, or conjugated to polysaccharides and/or other polymers for use in a vaccine formulation.

By virtue of the isolated proteins or polypeptides sharing a common epitope, it is believed that antibodies that recognize or bind to the shared epitope can be used to induce passive immunity against *Pneumocystis* organisms, *Streptococcus pneumoniae*, or both. The treatment or prevention of infection by one or both of these organisms can be carried out by administering to a patient an amount of an antibody of the present invention (i.e., recognize the isolated protein or polypeptides or the immunogenic conjugates of the present invention), or previously identified antibodies that recognize the epitope shared by *Pneumocystis* kexin and the protein of clone A12, or combinations thereof, where such antibodies are administered in an amount that is effective to treat or prevent infection by either a *Pneumocystis* organism, *Streptococcus pneumoniae*, or both.

Passive immunotherapy with antibody preparations have been used successfully in many infectious diseases. Because of the immunocompromised host's altered ability to respond to active immunization, passive immunotherapy is a way to provide the benefit of antibody without the necessity of a specific immune response in the recipient. While often used to prevent diseases, e.g., varicella immune globulin in the compromised host, it can be used therapeutically. The use of immunoglobulin has been shown to improve the outcome of CMV disease, particularly pneumonitis, and enteroviral encephalitis, in the immunocompromised human host (Ljungman, "Cytomegalovirus Pneumonia: Presentation, Diagnosis, and Treatment," *Semin. Respir. Infect.* 10(4):209-215 (1995); Dwyer et al., "Intraventricular Gamma-globulin for the Management of Enterovirus Encephalitis," *Pediatr. Infect. Dis. J.* 7(5 Suppl):S30-3 (1988), each of which is hereby incorporated by reference in its entirety). Animal models support this approach in a variety of fungal infections (Casadevall et al., "Return to the Past: The Case for Antibody-based Therapies in Infectious Diseases," *Clin. Infect. Dis.* 21(1):150-161 (1995), which is hereby incorporated by reference in its entirety).

According to one therapeutic embodiment, the antibody to be administered is an antibody raised against an isolated protein or polypeptide of the present invention.

According to another therapeutic embodiment, the antibody to be administered is an antibody raised against an immunogenic conjugate of the present invention.

According to a still further therapeutic embodiment, the antibody to be administered is monoclonal antibody 4F11, monoclonal antibody 1G4, or monoclonal antibody 4F11 (G1), all of which are identified in Gigliotti et al., "Passive Intranasal Monoclonal Antibody Prophylaxis Against Murine *Pneumocystis carinii* Pneumonia," *Infect. Immun.* 70:1069-1074 (2002), which is hereby incorporated by reference in its entirety).

In accordance with each of the above-identified methods of treating or preventing infection in a patient, the patient to be treated is preferably a mammal. Exemplary mammals to be treated include, without limitation, humans, horses, cows, pigs, orangutans, monkeys, rabbits, rats, or mice.

Regardless of the method of the present invention to be employed, i.e., either passive or active immunity, the immunopotency of a composition can be determined by monitoring the immune response of test animals following their immunization with the composition. Monitoring of the immune response can be conducted using any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

The immune response of the test subjects can be analyzed by various approaches such as: the reactivity of the resultant immune serum to the immunogenic conjugate or protein or polypeptide, as assayed by known techniques, e.g., enzyme linked immunosorbent assay ("ELISA"), immunoblots, immunoprecipitations, etc.; or, by protection of immunized hosts from infection by the pathogen and/or attenuation of symptoms due to infection by the pathogen in immunized hosts as determined by any method known in the art, for assaying the levels of an infectious disease agent, e.g., the bacterial levels (for example, by culturing of a sample from the patient), etc. The levels of the infectious disease agent may also be determined by measuring the levels of the antigen against which the immunoglobulin was directed. A decrease in the levels of the infectious disease agent or an amelioration of the symptoms of the infectious disease indicates that the composition is effective. Because the antibodies of the present invention recognize the commonly shared epitope from *Pneumocystis* and *Streptococcus pneumoniae*, the antibodies may not discriminate between these two antigens.

Generally, the therapeutics of the invention can be tested in vitro, and then in vivo, for the desired therapeutic or prophylactic activity, prior to use in humans. For example, in vitro assays that can be used to determine whether administration of a specific therapeutic is indicated include in vitro cell culture assays in which appropriate cells from a cell line or cells cultured from a patient having a particular disease or disorder are exposed to or otherwise administered a therapeutic, and the effect of the therapeutic on the cells is observed. Alternatively, the therapeutic may be assayed by contacting the therapeutic to cells (either cultured from a patient or from a cultured cell line) that are susceptible to infection by the infectious disease agent but that are not infected with the infectious disease agent, exposing the cells to the infectious disease agent, and then determining whether the infection rate of cells contacted with the therapeutic was lower than the infection rate of cells not contacted with the therapeutic. Infection of cells with an infectious disease agent may be assayed by any method known in the art. In addition, the therapeutic can be assessed by measuring the level of the molecule against which the antibody is directed in the animal model or human subject at suitable time intervals before, during, or after therapy. Any change or absence of change in the amount of the molecule can be identified and correlated with the effect of the treatment on the subject. The level of the molecule can be determined by any method known in the art.

After vaccination of an animal using the methods and compositions of the present invention, any binding assay known in the art can be used to assess the binding between the resulting antibody and the particular molecule. These assays may also be performed to select antibodies that exhibit a higher affinity or specificity for the particular antigen.

The antibodies or binding portions of the present invention are also useful for detecting in a sample the presence of the epitope of SEQ ID NO: 1 (or SEQ ID NOS: 7-24) and, therefore, the presence of either proteins containing the epitope of SEQ ID NO: 1 (or SEQ ID NOS: 7-24), as well as *Pneumocystis* or *Streptococcus pneumoniae*. This detection method includes the steps of providing an isolated antibody or binding portion thereof raised against an epitope containing SEQ ID NO: 1 (or SEQ ID NOS: 7-24), adding to the isolated antibody or binding portion thereof a sample suspected of containing a quantity of a protein or polypeptide that contains SEQ ID NO: 1 (or SEQ ID NOS: 7-24) or whole *Pneumocystis* or *Streptococcus pneumoniae*, and then detecting the presence of a complex comprising the isolated antibody or binding portion thereof bound to the epitope (or protein or polypeptide or whole organism, as noted above).

Immunoglobulins, particularly antibodies, (and functionally active fragments thereof) that bind a specific molecule that is a member of a binding pair may be used as diagnostics and prognostics, as described herein. In various embodiments, the present invention provides the measurement of a member of the binding pair, and the uses of such measurements in clinical applications. The immunoglobulins in the present invention may be used, for example, in the detection of an antigen in a biological sample whereby patients may be tested for aberrant levels of the molecule to which the immunoglobulin binds. By "aberrant levels" is meant increased or decreased relative to that present, or a standard level representing that present, in an analogous sample from a portion of the body or from a subject not having the disease. The antibodies of this invention may also be included as a reagent in a kit for use in a diagnostic or prognostic technique.

In an embodiment of the invention, an antibody of the invention that immunospecifically binds to an infectious disease agent, such as *Pneumocystis* or *Streptococcus pneumoniae*, or the proteins or polypeptides containing SEQ ID NO: 1 (or SEQ ID NOS: 7-24) may be used to diagnose, prognose or screen for the infectious disease or the proteins or polypeptides containing SEQ ID NO: 1 (or SEQ ID NOS: 7-24).

Examples of suitable assays to detect the presence of the epitope (i.e., proteins or polypeptides containing SEQ ID NO: 1 (or SEQ ID NOS: 7-24), *Pneumocystis*, or *Streptococcus pneumoniae*) include but are not limited to ELISA, radioimmunoassay, gel-diffusion precipitation reaction assay, immunodiffusion assay, agglutination assay, fluorescent immunoassay, protein A immunoassay, or immunoelectrophoresis assay.

The tissue or cell type to be analyzed will generally include those which are known, or suspected, to express the particular epitope. The protein isolation methods employed herein may, for example, be such as those described in Harlow and Lane (*Antibodies: A Laboratory Manual*, Cold Spring Harbor Laboratory Press, Cold Spring Harbor, N.Y. (1988), which is hereby incorporated by reference in its entirety). The isolated cells can be derived from cell culture or from a patient. The antibodies (or functionally active fragments thereof) useful in the present invention may, additionally, be employed histologically, as in immunofluorescence, immunohistochemistry, or immunoelectron microscopy, for in situ detection of the epitope or pathogens expressing the epitope. In situ detection may be accomplished by removing a histological specimen from a patient, such as paraffin embedded sections of affected tissues and applying thereto a labeled antibody of the present invention. The antibody (or functionally active fragment thereof) is preferably applied by overlaying the labeled an antibody onto a biological sample. If the molecule to which the antibody binds is present in the cytoplasm, it may be desirable to introduce the antibody inside the cell, for example, by making the cell membrane permeable. Through the use of such a procedure, it is possible to determine not only the presence of the particular molecule, but also its distribution in the examined tissue. Using the present invention, those of ordinary skill will readily perceive that any of a wide variety of histological methods (such as staining procedures) can be modified in order to achieve such in situ detection of the epitope of SEQ ID NO: 1 (or SEQ ID NOS: 7-24).

Immunoassays for the particular molecule will typically comprise incubating a sample, such as a biological fluid, a tissue extract, freshly harvested cells, or lysates of cultured cells, in the presence of a detectably labeled antibody and detecting the bound antibody by any of a number of techniques well-known in the art.

The biological sample may be brought in contact with and immobilized onto a solid phase support or carrier such as nitrocellulose, or other solid support which is capable of immobilizing cells, cell particles or soluble proteins. The support may then be washed with suitable buffers followed by treatment with the detectably labeled antibody. The solid phase support may then be washed with the buffer a second time to remove unbound antibody. The amount of bound label on solid support may then be detected by conventional means. "Solid phase support or carrier" includes any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given antibody may be determined according to well known methods. Those skilled in the art will be able to determine operative and optimal assay conditions for each determination by employing routine experimentation.

One of the ways in which an antibody can be detectably labeled is by linking the same to an enzyme and use in an enzyme immunoassay (EIA) (Voller, "The Enzyme Linked Immunosorbent Assay (ELISA)," Diagnostic Horizons 2:1-7, Microbiological Associates Quarterly Publication, Walkersville, Md. (1978); Voller et al., *J. Clin. Pathol.* 31:507-520 (1978); Butler, *Meth. Enzymol.* 73:482-523 (1981); Maggio, E. (ed.), *Enzyme Immunoassay*, CRC Press, Boca Raton, Fla. (1980); Ishikawa et al., (eds.), *Enzyme immunoassay*, Kgaku Shoin, Tokyo (1981), each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the synthetic antibodies or fragments, it is possible to detect the protein that the antibody was designed for through the use of a radioimmunoassay (RIA) (see, e.g., Weintraub, *Principles of Radioimmunoassays*, Seventh Training Course on Radioligand Assay Techniques, The Endocrine Society (1986), each of which is hereby incorporated by reference). The radioactive isotope can be detected by such means as the use of a gamma counter or a scintillation counter or by autoradiography. It is also possible to label the antibody with a fluorescent compound or semiconductor nanocrystals. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. A number of various semiconductor nanocrystals (i.e., nanodots) ocan be selected. Chemiluminescent compounds can alternatively be coupled to the antibodies. The presence of the chemiluminescent-tagged antibody is determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound may be used to label the synthetic antibody of the present invention. Bioluminescence is a type of chemiluminescence found in biological systems, in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

An additional aspect of the present invention relates to diagnostic kits for the detection or measurement of proteins or polypeptides containing the epitope of SEQ ID NO: 1 (or SEQ ID NOS: 7-24) or whole organisms expressing such epitope. Kits for diagnostic use are provided that contain in one or more containers an anti-SEQ ID NO: 1 (or SEQ ID NOS: 7-24) antibody, and, optionally, a labeled binding partner to the antibody. Alternatively, the anti-SEQ ID NO: 1 (or SEQ ID NOS: 7-24) antibody can be labeled (with a detectable marker, e.g., a chemiluminescent, enzymatic, fluorescent, or radioactive moiety). Accordingly, the present invention provides a diagnostic kit includes an anti-SEQ ID NO: 1 (or SEQ ID NOS: 7-24) antibody and a control immunoglobulin. In a specific embodiment, one of the foregoing compounds of the container can be detectably labeled. A kit can optionally further include in a container, for use as a standard or control, a predetermined amount of a protein or polypeptide that contains the epitope of SEQ ID NO: 1 (or SEQ ID NOS: 7-24) and therefore is recognized by the said antibody of the kit.

EXAMPLES

The following examples are provided to illustrate embodiments of the present invention but are by no means intended to limit its scope.

Materials and Methods for Example 1-8

Oligonucleotide Annealing and PCR

The oligonucleotides used in this study are listed in Table 1 below.

TABLE 1

Oligonucleotides used in this study

| Construct Name | Oligo Name | SEQ ID NO: | Sequence |
|---|---|---|---|
| Kexin$_{856-872}$THIO | Kexin Epitope S | 25 | aaaccggcacctaaaccaaca ccacctaaaccagcgcctaaa ccagcaccaa |
| Kexin$_{356-872}$THIO | Kexin Epitope AS | 26 | tggtgctggtttaggcgctgg tttaggtggtgttggtttagg tgccggttta |
| Kexin$_{777-787}$THIO | A39 Epitope2 S | 27 | agaccagcaccacctaaacca acacctcaaccaa |
| Kexin$_{777-787}$THIO | A39 Epitope2 AS | 28 | tggttgaggtgttggtttagg tggtgctggtcta |
| Kexin$_{856-863}$THIO | A32.1 Epitope S | 29 | aaaccggcacctaaaccaaca ccaa |
| Kexin$_{856-363}$THIO | A32.1 Epitope AS | 30 | tggtgttggtttaggtgccgg ttta |
| Kexin$_{865-872}$THIO | A32.2 Epitope S | 31 | aaaccagcgcctaaaccagca ccaa |
| Kexin$_{865-872}$THIO | A32.2 Epitope AS | 32 | tggtgctggtttaggcgctgg ttta |
| Kexin$_{860-868}$THIO | A32.3 Epitope S | 33 | aaaccaacaccacctaaacca gcgccta |
| Kexin$_{860-868}$THIO | A32.3 Epitope AS | 34 | aggcgctggtttaggtggtgt tggttta |
| Kex Epi 5' | pSCREEN T7 10 S | 35 | ctgggtaaggagattattgcg |
| Kex Epi 5' | A32 Epitope AS2 | 36 | tggtgctggtttaggcgctgg |
| Kex Epi 3' | A32 Epitope S3 | 37 | tctaaatcatcatctaaacca acatc |
| Kex Epi 3' | pSCREEN T7 10 AS | 38 | cgcaagcttgtcgacggag |
| A12$_{62-77}$THIO | A12 Epitope S | 39 | aaacctcgacctcagccaacg tcaaaacctcgacctcagccg acgccaa |
| A12$_{62-77}$THIO | A12 Epitope AS | 40 | tggcgtcggctgaggtcgagg ttttgacgttggctgaggtcg aggttta |
| A12$_{70-77}$THIO | A12.2 Epitope 5 | 41 | aaacctcgacctcagccgacg ccaa |
| A12$_{70-77}$THIO | A12.2 Epitope AS | 42 | tggcgtcggctgaggtcgagg ttta |
| A12$_{46-53}$THIO | A12'2 Epitope S | 43 | gaacctcgacctcagccgacg tcaa |
| A12$_{46-53}$THIO | A12'2 Epitope AS | 44 | tgacgtcggctgaggtcgagg ttca |
| A12$_{54-61}$THIO | A12'3 Epitope S | 45 | gaacctcagcctcagccggcg ccaa |
| A12$_{54-61}$THIO | A12'3 Epitope AS | 46 | tggcgccggctgaggctgagg ttca |
| A12$_{18-21/11-42}$THIO | A12 S | 47 | accaatatatccgaaccagc |
| A12$_{1-142}$THIO | A12 Mid AS | 48 | ttctgatgttgactgagatgg |
| A12$_{1-82}$THIO | A12 Mid AS2 | 49 | ccgacgccagaaacctcg |

TABLE 1-continued

Oligonucleotides used in this study

| Construct Name | Oligo Name | SEQ ID NO: | Sequence |
|---|---|---|---|
| A12 Sequence | Lambda forward | 50 | tggcgacgactcctggagcccg |
| A12 Sequence | Lambda reverse | 51 | tgacaccagaccaactggtaatgg |
| URSP2 PspA seq | PspA S2 | 52 | gcaagcttatgatatagaaatttgtaac |
| URSP2 PspA seq | PspA AS | 53 | ccacataccgttttcttgtttccagcc |
| URSP2 PspA:THIO | PspA S3 | 54 | acaagtctagccagctcgc |
| URSP2 PspA:THIO | PspA AS | 55 | ccacataccgttttcttgtttccagcc |

SEQ ID NOS: 52-55 (PspA) were obtained from sequences reported in Hollingshead et al., "Diversity of PspA: Mosaic Genes and Evidence for Past Recombination in *Streptococcus pneumoniae*," *Infect. Immun.* 68:5889-5900 (2000), which is hereby incorporated by reference in its entirety.

Complementary oligonucleotides were purchased from Sigma-Genosys (Woodlands, Tex.). Lyophilized oligonucleotides were resuspended in annealing buffer (10 mM Tris, pH 8.0, 50 mM NaCl, 1 mM EDTA) at 100 pmol/mL. Twenty-five μL of each were mixed and heated to 95° C. for 2 min then cooled to 25° C. at a rate of 0.02° C./sec using a PCR Sprint Thermocycler (Hybaid Ashford, UK). Annealed oligonucleotides were electrophoresed on a 2% agarose gel and purified using the Qiaquick gel extraction kit (Qiagen Valencia, Calif.), then used immediately in DNA ligations. PCR conditions were as follows: 90 sec at 95° C.; 90 sec at ($T_M$ lower-4° C.) where $T_M$ lower signifies the lower melting temperature of each primer pair; 2 min at 72° C. for 30 cycles with a 10 min 72° C. final extension step for addition of 3' overhangs by Taq polymerase.

Bacterial Strains, Growth Conditions, Plasmid Isolation and Nucleotide Sequencing:

PCR amplified Kex1 or annealed complementary Kex1 or A12 oligonucleotide inserts (see Table 1 above) were cloned into TOPO TA cloning vectors (Invitrogen Co., Carlsbad, Calif.) following the manufacturer's instructions. *E. coli* transformants were grown at 37° C. in Luria-Bertani (LB) medium with 100 μg/mL ampicillin. For colony immunoscreens, *E. coli* transformants were grown on LB agar plates+100 μg/mL ampicillin+50 μg/mL tetracycline. *S. pneumoniae* strains were obtained from the Strong Memorial Hospital Clinical Microbiology Laboratory at the University of Rochester. *S. pneumoniae* was grown at 37° C. on trypticase soy agar II-5% sheep blood agar plates or in Todd-Hewitt broth+5% yeast extract (THY). Plasmid DNA was isolated from *E. coli* using a Qiagen miniprep kit; both strands of each cloned insert were sequenced by the University of Rochester Core Nucleic Acid Sequencing Facility. *S. pneumoniae* chromosomal DNA was isolated as described (Chen et al., "*Streptococcus salivarius* Urease: Genetic and Biochemical Characterization and Expression in a Dental Plaque *Streptococcus*," *Infect. Immun.* 64:585-592 (1996), which is hereby incorporated by reference in its entirety).

Immunodetection Assays:

MAb 4F11 was produced as described (Lee et al., "Molecular Characterization of KEX1, a Kexin-Like Protease in Mouse *Pneumocystis carinii*," *Gene* 242:141-150 (2000), which is hereby incorporated by reference in its entirety). For colony immunoscreens and *P. carinii* immunofluorescence assays (IFAs), mAb 4F11 IgM ascites fluid was used at a 1:5000 dilution. For enzyme-linked immunosorbent assays (ELISA) and Western blots of purified recombinant proteins an $IgG_1$ switch-variant of mAb 4F11($G_1$) (Gigliotti et al., "Passive Intranasal Monoclonal Antibody Prophylaxis Against Murine *Pneumocystis carinii* Pneumonia," *Infect. Immun.* 70:1069-1074 (2002), which is hereby incorporated by reference in its entirety) was prepared by saturated ammonium sulfate precipitation of tissue culture supernatant and used at the indicated dilutions. MAb 2B5 is an $IgG_1$ that recognizes a mouse *P. carinii* gpA (Gigliotti et al., "Antibody-Mediated Shift in the Profile of Glycoprotein A Phenotypes Observed in a Mouse Model of *Pneumocystis carinii* Pneumonia," *Infect. Immun.* 64:1892-1899 (1996), which is hereby incorporated by reference in its entirety) and was used as a negative control in *S. pneumoniae* immunoblots and IFAs. MAb 1C7 is an anti-mouse *P. carinii* IgM used as an isotype control in IFAs against *P. carinii* derived from different hosts. Pooled hyperimmune sera against mouse *P. carinii* was obtained as described previously (Gigliotti et al., "Development of Murine Monoclonal Antibodies to *Pneumocystis carinii*," *J. Infect. Dis.* 154:315-322 (1986), which is hereby incorporated by reference in its entirety).

Purified recombinant protein at a concentration of 10 μg/mL in 50 mM carbonate-bicarbonate buffer pH 9.5+0.1% SDS was used to coat Costar ELISA plates (Corning Incorporated, Corning, N.Y.) 16-20 hr at 37° C. The plates were blocked with 3% BSA-TBST for 1 hr at 4° C. Primary antibody was added in two-fold serial dilutions in 3% BSA-TBST and incubated at 4° C. for 1 hr. Goat anti-mouse IgG+IgM-alkaline phosphatase conjugate secondary antibody was added at 1:5000 dilution in BSA-TBST for one hr at 4° C. Blue Phos substrate (KPL, Gaithersburg Md.) was added for 30 min, color development was stopped with 2.5% EDTA, and absorbance was read at 655 nM using a Benchmark microplate reader (Bio-Rad).

Mouse *P. carinii* Kexin 777-787 (RPAPPKPTPQP, SEQ ID NO: 56) and Kexin 131-142 (SGDTGNVNSGEK, SEQ ID NO: 57) peptides were purchased from Alpha Diagnostics (San Antonio, Tex.). ELISA experiments using the synthetic peptides were performed as described above, using 10 µg peptide/mL in carbonate-bicarbonate buffer to coat the plates. For competitive ELISA studies peptides were incubated at three fold dilutions with a starting concentration of 100 µg/mL for 2 hr with a 1:3200 dilution of mAb 4F11 at 4° C. to reach equilibrium. Mouse P. carinii sonicates in carbonate-bicarbonate buffer were used to coat ELISA plates at the equivalence of $4 \times 10^4$ cysts per well overnight at 4° C. The peptide-antibody mixtures, or antibody alone at 1:3200 dilution, were used as the primary antibody in the ELISA following the above protocol.

P. carinii IFA were performed as described (Gigliotti et al., "Development of Murine Monoclonal Antibodies to Pneumocystis carinii," J. Infect. Dis. 154:315-322 (1986), which is hereby incorporated by reference in its entirety). S. pneumoniae was swabbed from blood agar plates after overnight growth at 37° C. and resuspended in 1.5 mL PBS+3% fetal calf serum (PBS-FCS). Cells were pelleted by centrifugation at 1000×g, resuspended in 1.5 mL PBS-FCS and 0.5 mL aliquots were placed into 3 microcentrifuge tubes to which either 0.5 mL of mAb 4F11 IgG$_1$ tissue culture supernatant, mAb 2B5, or TBS-FCS alone was added. After 2 hr incubation at room temperature with rotation, cells were washed twice with PBS-FCS and incubated with goat-anti mouse IgG FITC-conjugated antibody (Molecular Probes Inc., Eugene Oreg.) for 30 min in the dark with rotation. The cells were washed three times with PBS-FCS and resuspended in 100 µL PBS-FCS. Five µL of the suspension was allowed to dry on slides overnight in the dark. Immunofluorescence was visualized using an Olympus BX41 microscope (Olympus America, Melville N.Y.) with a fluorescein filter cube. Images were captured using a Retiga digital camera and Q capture 2.0 software (QImaging, Burnaby, BC) and processed using Adobe Photoshop ver. 6.01 (Adobe Systems, San Jose, Calif.).

To confirm reactivity of E. coli pSCREEN transformants with mAb 4F11, 5 mL overnight cultures were pelleted and resuspended in 200 µL of 1× Laemmli SDS running/sample buffer+5% β-mercaptoethanol, and 20 µL samples were separated on NuPAGE Bis-Tris 4-12% gels (Invitrogen) by SDS-PAGE. S. pneumoniae from blood agar plates was grown in 5 mL THY overnight, 1 mL aliquots were pelleted, resuspended in 200 µL 1× sample buffer, and 20 µL were resolved by SDS-PAGE. Purified recombinant protein was suspended in sample buffer in equal concentrations and separated as described for cell lysates. Western blots were performed as previously described (Lee et al., "Molecular Characterization of KEX1, a Kexin-Like Protease in Mouse Pneumocystis carinii," Gene 242:141-150 (2000), which is hereby incorporated by reference in its entirety).

Epitope Mapping:

The epitope recognized by mAb 4F11 within mouse P. carinii Kex1 was mapped using the Novatope system (Novagen Madison Wis.) following the manufacturer's instructions. Briefly, 30 µg of plasmid A32:pTrcHIS, which contains the C-terminal 620 residues of the mouse P. carinii Kex1 cDNA (Lee et al., "Molecular Characterization of KEX1, a Kexin-Like Protease in Mouse Pneumocystis carinii," Gene 242:141-150 (2000), which is hereby incorporated by reference in its entirety) was partially digested with DNaseI and fragments were separated by agarose gel electrophoresis. Fragments between 50-150 bp were gel-purified, the ends of the fragments filled-in using T4 polymerase, and single-stranded deoxyriboadenylate tails were added to the 3' ends using Tth polymerase. Fragments were then ligated into the linearized pSCREEN T-vector, which contains 5' thymidine overhangs and used to transform E. coli Nova Blue cells. Following an overnight incubation at 37° C., transformants were lifted onto nitrocellulose filters, lysed in a chloroform vapor chamber, and denatured with 6M urea. Filters were then processed analogous to a Western blot (see below). Positive reactivity to mAb 4F11 of selected clones was confirmed by Western blot of boiled lysates.

Recombinant Protein Expression and Purification:

Production of 6×His-tagged thioredoxin fusion proteins using the pBADTHIO expression system in E. coli was performed following the manufacturer's instructions. Briefly, overnight cultures were diluted 1:40 in fresh LB+100 µg/mL ampicillin and grown at 37° C. with shaking to absorbance at 600 nm of approximately 0.5. For fusion protein induction, arabinose was added to a final concentration of 0.02% and cultures were grown an additional 5 hr at 37° C. with shaking. Cells were pelleted by centrifugation at 1000×g then resuspended in ⅕ original culture volume with lysis buffer (50 mM sodium phosphate, 6 M guanidine-HCl, 300 mM NaCl) and vortexed vigorously. Debris was pelleted by centrifugation at 10,000×g at 4° C. The supernatants were passed over a TALON affinity resin column (BD Biosciences, Palo Alto, Calif.) that had been pre-equilibrated with lysis buffer. The columns were then washed twice with 10 mL 50 mM sodium phosphate, 300 mM NaCl. The fusion proteins were eluted with 2 mL buffer containing 50 mM sodium phosphate, 300 mM NaCl, and 150 mM imidazole. The eluted protein was dialyzed overnight against PBS at 4° C. and concentrated by vacuum centrifugation. Protein concentrations were determined using a BCA microwell assay kit (Pierce, Rockford, Ill.).

Purification of Native P. carinii Antigen Recognized by mAb 4F11:

The mAb 4F11 affinity column was prepared using 4F11 (G$_1$) and REACTIGEL resin (Pierce) following the manufacturer's instructions. Briefly, 10 mL of 1.7 mg/mL 4F11(G1) were coupled to 3 mL 6× REACTIGEL overnight at 4° C. The supernatant was removed, the resin was blocked with pH 9.0 1.0 Methanolamine and washed with PBS prior to use. P. carinii antigens recognized by mAb 4F11 were purified from 1 mL sonicated P. carinii-infected SCID mouse lung homogenates ($8 \times 10^6$ organisms) by passage over the mAb 4F11 affinity column five times, followed by 2 washes with 10 mL PBS and elution with pH 2.5 100 mM glycine buffer.

Statistical Analysis:

Experimental ELISA results were statistically compared to the control values using a two-tailed Student's t test. Results were considered significant if $p \leq 0.05$.

GenBank Accession Numbers, BLAST Searches and Protein Sequence Alignment:

The GenBank Accession numbers for sequences presented in the text are as follows: mouse P. carinii cDNA clone A12, AY371664; URSP PspA clade defining region and proline-rich repeat, AY371665. Each of these GenBank Accessions is hereby incorporated by reference in its entirety. Searches for short, nearly-exact matches to the kexin 17-mer mAb 4F11 epitope in GenBank were conducted using the BLASTp database search algorithm (Altschul et al., "Gapped BLAST and PSI-BLAST: A New Generation of Protein Database Search Programs," Nucleic Acids Res 25:3389-3402 (1997), which is hereby incorporated by reference in its entirety). The Kexin$_{856-872}$ and Kexin$_{777-787}$ mAb 4F11 epitopes were aligned with the deduced amino acid sequence of the PspA proline rich repeat region using the Genetics Computer Group Genesys software (GCG, University of Rochester) (Pearson et al., "Improved Tools for Biological Sequence Comparison," *Proc. Natl. Acad. Sci. USA* 85:2444-2448 (1988), which is hereby incorporated by reference in its entirety).

Cloning and Expression of a *Streptococcus pneumoniae* PspA Fragment:

Conserved primers (Table 1 above and Hollingshead et al., "Diversity of PspA: Mosaic Genes and Evidence for Past Recombination in *Streptococcus pneumoniae*," *Infect. Immun.* 68:5889-5900 (2000), which is hereby incorporated by reference in its entirety) were used to PCR amplify and sequence a portion of the *S. pneumoniae* strain URSP2 PspA gene. Using primers derived from the PspA sequence obtained, an in-frame fragment encoding the N-terminal alpha helical domain through the proline-rich repeat region of the molecule was cloned into thioredoxin fusion vector pBADTHIO (Invitrogen) for recombinant polypeptide expression.

Example 1 mAb 4F11 Recognizes *P. carinii* from Different Hosts

The mAbs 4F11 and 1C7, which were derived from mice immunized with mouse *P. carinii*, were used as probes against *P. carinii* isolates derived from mice, rats, ferrets, Rhesus macaques, and humans (also termed *P. jiroveci*). As shown in FIG. 1, mAb 4F11 recognized antigens on the surface of *P. carinii* derived from all five host species. However, the isotype-matched mAb, 1C7, was only capable of recognizing mouse *P. carinii*, the organism used as the immunogen, a characteristic of most anti-*P. carinii* antibodies (Gigliofti et al., "*Pneumocystis carinii* Host Origin Defines the Antibody Specificity and Protective Response Induced by Immunization," *J. Infect. Dis.* 176:1322-1326 (1997), which is hereby incorporated by reference in its entirety). The pattern and intensity of fluorescent staining suggests that the epitope recognized by mAb 4F11 is abundant on the surface of *P. carinii* cysts, and possibly on the trophic form of the organism, which may be represented by the smaller highly fluorescent particles seen in FIG. 1.

Example 2

Identification of Mouse *P. carinii* Kex1 Epitope Recognized by mAb 4F11

A cDNA clone (A32) encoding the C-terminal 200 amino acid residues of *P. carinii* Kex1 (Lee et al., "Molecular Characterization of KEX1, a Kexin-Like Protease in Mouse *Pneumocystis carinii*," *Gene* 242:141-150 (2000), which is hereby incorporated by reference in its entirety) was used to construct a shotgun cleavage library in *E. coli*; colony immunoscreening was performed with mAb 4F11. Positive clones were confirmed by Western blotting. Inserts from the plasmids of three positive clones were sequenced and shown to contain the 27 amino acid region underlined in FIG. 2A. The epitope mapped to the junction of the proline-rich domain and serine/threonine rich domain of the kexin molecule. To further delineate the epitope, two fusion proteins were analyzed, one containing the first 17 amino acids (Pro-rich domain residues 856-872) and the other the last 10 amino acids (Ser/Thr-rich domain residues 873-882) of the 27-mer epitope region, in Western blots using mAb 4F11 and an expression control antibody. It was determined that the epitope recognized by mAb 4F11 resides within the first 17 amino acids of the 27-mer.

Example 3

Identification of Additional Mouse *P. carinii* Protein Recognized by mAb 4F11

In Western blots of *P. carinii*-infected mouse lung homogenates, several bands are detected by mAb 4F11 (Gigliotti et al., "Passive Intranasal Monoclonal Antibody Prophylaxis Against Murine *Pneumocystis carinii* Pneumonia," *Infect. Immun.* 70:1069-1074 (2002), which is hereby incorporated by reference in its entirety). A previous immunoscreen of a mouse *P. carinii* cDNA expression library in λgt11 identified multiple clones containing inserts that encode proteins recognized by mAb 4F11. The primary structure of clone A12 is distinct from mouse *P. carinii* Kex1 and encodes a 278 amino acid polypeptide that is rich in proline residues. Clone A12 appears to encode the C-terminal portion (SEQ ID NO: 5) of its respective protein based on the presence of a stop codon and poly-A tail in the nucleotide sequence of the cDNA (FIG. 2B). Outside of the proline-rich region, there is no significant homology between the A12 polypeptide and either *P. carinii* Kex1 or any other protein in the available databases. A hydrophobic C-terminus in the A12 polypeptide suggests that the mature protein may be membrane anchored and the high proline content suggests that the molecule may be cell wall-associated (Briles et al., "Role of Pneumococcal Surface Protein A in the Virulence of *Streptococcus pneumoniae*." *Rev. Infect. Dis.* 10 Suppl 2:S372-S374 (1988); Harmsen et al., "Active Immunity to *Pneumocystis carinii* Reinfection in T-cell-depleted Mice," *Infect. Immun.* 63:2391-2395 (1995), each of which is hereby incorporated by reference in its entirety).

Example 4

Identification of the Region of Mouse *P. carinii* cDNA Clone A12 Containing the mAb 4F11 Epitope Alignment of the *P. carinii* Kex1 mAb 4F11 epitope with the deduced amino acid sequence of clone A12 (SEQ ID NO: 5) revealed no obvious matches, though some areas of similarity in charge distribution and proline content were observed. To identify the region of the molecule recognized by mAb 4F11, truncated forms of the A12 molecule were expressed as thioredoxin fusion proteins. Constructs containing amino acid residues 1-142 and 1-82 of SEQ ID NO: 5 (FIG. 3B) both reacted with mAb 4F11, while the fusion partner alone was detected by the epitope tag mAb but did not react with mAb 4F11 (FIGS. 3A-B). These results narrowed the mAb 4F11 epitope to the first 82 amino acids of SEQ ID NO: 5 encoded by clone A12.

Example 5

Recognition of Recombinant A12 Fusion Protein and mAb 4F11 Immunopurified Native *P. carinii* Antigens by Hyperimmune Sera from *P. carinii*-Immunized Mice The fusion protein containing the first 82 amino acids of SEQ ID NO: 5 encoded by cDNA clone A12 also reacted with hyperimmune sera from mice immunized with whole *P. carinii* (FIG. 3C), but not with sera from un-immunized mice (FIG. 3D). This demonstrates that antibodies are made against the mAb 4F11 epitope-containing region of the A12 protein during a protective response to *P. carinii*. The anti-*P. carinii* antisera also recognized *P. carinii* antigen(s) from the lungs of SCID mice purified using a mAb 4F11 affinity column (FIG. 3F). The faintness of the band recognized in the mAb 4F11 affinity column compared to *P. carinii* infected mouse lung homogenates is likely due to the low concentration of antigen recovered in the purification process as determined by the inability to detect similarly loaded antigen in silver stained SDS PAGE gels.

Example 6

Fine Structure Analysis of the mAb 4F11 Epitope Constructs in Mouse *P. carinii* Kex1 and Clone A12

Further examination of both the mouse *P. carinii* Kex1 and A12 sequences revealed a number of near-matches to the Kex1 17-mer epitope identified in the immunoscreen. To determine the sequence constraints of the different possible mAb 4F11 epitopes in Kex1 and A12, fusion proteins containing several of the putative epitopes were made. An alignment of the fusion protein inserts based on conservation of the positions of their proline residues is shown in FIG. 4.

$Kexin_{856-872}$ contains the 17-mer identified in the original immunoscreen ($K_{856}$PAPKPTPPKPAPKPAP$_{872}$, SEQ ID NO: 58). The $A12_{62-77}$ construct ($K_{62}$PRPQPTSKPRPQPTP$_{77}$, SEQ ID NO: 59) was chosen because it was the nearest match to the Kex1 17-mer within the N-terminal 82 residues shown to contain a mAb 4F11 epitope (FIG. 3B). The homologous $Kexin_{777-787}$ construct ($R_{777}$PAPPKPTPQP$_{787}$, SEQ ID NO: 56) is located upstream of the region encoded by cDNA clone A32. Because $Kexin_{856-872}$ and the sequence upstream of this region consists of several near-exact repeats of 8 or 9 amino acids, three overlapping constructs, $Kexin_{856-863}$ ($K_{856}$PAPKPTP$_{863}$, SEQ ID NO: 60), $Kexin_{865-872}$ ($K_{865}$PAPKPAP$_{872}$, SEQ ID NO: 61) and $Kexin_{860-868}$ ($K_{860}$PTPPKPAP$_{868}$, SEQ ID NO: 62) were made in an attempt to narrow the epitope further. Three 8-mer fusions were also designed from the A12 sequence, one of which had high similarity to the kexin 8-mers ($A12_{70-77}$; $K_{70}$PRPQPTP$_{77}$, SEQ ID NO: 63). The other two A12 8-mers had charge substitutions at the first position to determine whether a basic residue was required at this position ($A12_{46-53}$, $E_{46}$PRPQPTS$_{53}$, SEQ ID NO: 64; and $A12_{54-61}$, $E_{54}$PQPQPAP$_{61}$, SEQ ID NO: 65).

When 1 µg of each of the purified proteins was separated by SDS-PAGE, the recombinant protein was the only band visible by Coomassie staining (FIG. 5A). Western blots of gels run in parallel showed that $A12_{46-53}$ and $A12_{54-61}$, which contain negatively charged glutamic acid residues in the first position, do not react with mAb 4F11, whereas all other constructs that contain positively charged amino acid residues at the first position react with mAb 4F11. These blots also show that the thioredoxin fusion partner alone does not react with mAb 4F11, yet all constructs and the thioredoxin control show equal reactivity to the anti-V5 antibody which recognizes an epitope within the fusion partner (FIGS. 5B and C). The positive reactivity of $A12_{70-77}$, $Kexin_{856-863}$ and $Kexin_{865-872}$ with mAb 4F11 suggests that mAb 4F11 could recognize an 8 amino acid peptide. An unanticipated observation was that the $Kexin_{777-787}$ showed enhanced binding with mAb 4F11 than the original epitope identified, $Kexin_{856-872}$, based on the size and intensity of the band detected by Western blot. Since this sequence of mouse *P. carinii* kexin falls upstream of the A32 cDNA clone encoded region used in the mapping experiments, it was not identified by the original epitope mapping strategy. The consensus 8-mer epitope recognized by mAb 4F11 is consistent with SEQ ID NO: 1, though additional substitutions in the longer epitopes still allow recognition by mAb 4F11. For example, $Kexin_{777-787}$ and $Kexin_{860-868}$ contain an additional proline residue at the fifth position and $Kexin_{777-787}$ has a charge-conserved arginine at the first position instead of a lysine.

To further evaluate the ability of mAb 4F11 to recognize the larger fusion constructs, ELISA experiments were performed using a mAb 4F11($G_1$) switch variant or anti-V5 epitope tag control antibody. As shown in FIG. 5D, $Kexin_{856-872}$ and $Kexin_{777-787}$ showed highest reactivity with mAb 4F11 at lower dilutions, whereas $A12_{62-77}$ showed lower reactivity, but significantly higher than the thioredoxin fusion partner alone (p≦0.05). At higher mAb 4F11 dilutions $Kexin_{777-787}$ showed greater reactivity with mAb 4F11 than did the original 17mer epitope, which is in agreement with the Western blot data. At 1:800 or greater dilution, the A12 16-mer showed only background reactivity to mAb 4F11 suggesting that this is the weakest binder of the three epitopes tested.

To confirm the specificity of mAb 4F11 to the epitope of highest apparent affinity ($Kex_{777-787}$) in the absence of a fusion partner, a synthetic peptide was used in ELISA experiments. The control peptide, (Kex131-142: SGDTGNVNS-GEK, SEQ ID NO: 57) did not react with mAb 4F11, whereas $Kex_{777-787}$ showed high reactivity to mAb 4F11 (FIG. 5E). In an inhibition ELISA, $Kexin_{777-787}$ was able to completely block binding of mAb 4F11 to native *P. carinii* antigens at concentrations as low as 1 µg/mL, and showed 50% inhibition of binding at 150 ng/mL, whereas Kex131-142 showed no inhibition at the highest concentration tested (FIG. 5F).

Example 7

Identification of a *Streptococcus pneumoniae* PspA Surface Protein Isoform that is Recognized by mAb 4F11

BLAST searches (Altschul et al., "Gapped BLAST and PSI-BLAST: A New Generation of Protein Database Search Programs," *Nucleic Acids Res.* 25:3389-3402 (1997), which is hereby incorporated by reference in its entirety) of GenBank for short nearly exact matches to the Kex1 17mer corresponding to the Ab 4F11 epitope revealed a number of proline-rich protein sequences in microbes and plants, but none in mammals. One of these sequences, *S. pneumoniae* PspA (GenBank Accession AAF70097, which is hereby incorporated by reference in its entirety), also contained a large number of lysine residues with similar periodicity to the lysines in $Kexin_{856-872}$. This proline-lysine repeat motif appears in the majority of isoforms of PspA from different *S. pneumoniae* strains (Hollingshead et al., "Diversity of PspA: Mosaic Genes and Evidence for Past Recombination in *Streptococcus pneumoniae*," *Infect Immun.* 68:5889-5900 (2000), which is hereby incorporated by reference in its entirety). To determine whether mAb 4F11 was capable of recognizing epitopes on the pneumococcal surface, IFA were performed on four clinical reference strains of *S. pneumoniae*. All four isolates showed positive staining with mAb 4F11 by IFA, but one strain, URSP2, demonstrated intense reactivity (FIG. 6A). This isolate was chosen for further analysis. To confirm the reactivity between *S. pneumoniae* and mAb 4F11, extracts of URSP2 cells were analyzed by SDS-PAGE and Western blotting with mAb 4F11. As shown in FIG. 6B, lane 3, a single band with a migration of approximately 90 kDa in the *S.* pneumoniae lysate lane was recognized by mAb 4F11. This band is within the reported size range of *S. pneumoniae* PspA isoforms (Tart et al., "Truncated *Streptococcus pneumoniae* PspA Molecules Elicit Cross-Protective Immunity Against Pneumococcal Challenge in Mice," *J. Infect. Dis.* 173:380-386 (1996), which is hereby incorporated by reference in its entirety).

A portion of URSP2 PspA containing the nucleotide sequence encoding the proline-rich domain was cloned and sequenced. The deduced amino acid sequence of the PspA fragment was shown to contain a repetitive 88 amino acid stretch with two regions of 80% or greater similarity to $Kexin_{856-872}$ and three regions with 80% or greater similarity to $Kexin_{777-787}$ (FIG. 7). These two Kex1 epitopes showed the strongest reactivity to mAb 4F11 by Western blotting and ELISA (FIGS. 5B, 5D). Purified recombinant thioredoxin fusion protein containing the α-helical domain, clade defining region, and proline-rich repeat region of URSP2 PspA was shown to react with mAb 4F11 (FIG. 6C). The thioredoxin fusion partner alone did not react with mAb 4F11 but did react with the anti-V5 epitope tag mAb (FIGS. 6C-D). This strongly suggests that the band recognized by mAb 4F11 in Western blots of whole cell extracts of URSP2 is PspA.

Example 8

Mab 4F11 Protects Against *S. pneumoniae* Bacteremia

To determine whether there is biologic significance to the crossreactive recognition of *S. pneumoniae* by mab 4F11, a mouse model of *S. pneumoniae* pneumonia and bacteremia was used. For these studies, six mice were given 150-200 µg of mab 4F11(G1), the IgG1 switch variant of the IgM 4F11 mab, ip, and 24 hours later *S. pneumoniae* were instilled into their trachea. Twenty-four hours following instillation, the mice were sacrificed and bacterial colony counts in the blood were determined. Control mice received an isotype-matched irrelevant mab. Passive administration of mab 4F11(G1) reduced colony counts in the blood by 99.9%. The concentration of pneumococci in the six control mice was $2\times10^4$ cfu/ml compared to $7\times10$ cfu/ml in the six mice protected with mab 4F11(G1). Thus, this mab passively protected against two completely different infectious diseases supporting the biologic significance of this antigen-antibody interaction. Applicants would like to note, however, that efforts to reproduce these results in an independent laboratory have not yet proven successful.

Discussion of Examples 1-8

The foregoing experimental work demonstrates the ability of mAb 4F11 to recognize *P. carinii* derived from multiple hosts (FIG. 1), and its ability to recognize antigens other than the immunodominant surface antigen, gpA (Gigliotti et al., "Glycoprotein A is the Immunodominant Antigen of *Pneumocystis carinii* in Mice Following Immunization," *Parasitol Res.* 82:90-91 (1996); Lee et al., "Molecular Characterization of KEX1, a Kexin-Like Protease in Mouse *Pneumocystis carinii*," *Gene* 242:141-150 (2000), each of which is hereby incorporated by reference in its entirety), separates mAb 4F11 from most anti-*P. carinii* antibodies (Gigliotti et al., "Recognition of *Pneumocystis carinii* Antigens by Local Antibody-Secreting Cells Following Resolution of *P. carinii* Pneumonia in Mice," *J. Infect. Dis.* 178:235-242 (1998); Gigliotti et al., "Antigenic Characterization of *Pneumocystis carinii*," *Semin. Respir. Infect.* 13:313-322 (1998), each of which is hereby incorporated by reference in its entirety). MAb 4F11 takes on added importance because of its ability to confer passive prophylaxis against PCP in a mouse model (Gigliotti et al., "Passive Intranasal Mono clonal Antibody Prophylaxis Against Murine *Pneumocystis carinii* Pneumonia," *Infect Immun* 70:1069-1074 (2002), which is hereby incorporated by reference in its entirety). The above examples describe the mapping of a number of similar peptide epitopes recognized by mAb 4F11 within two different *P. carinii* antigens. BLAST searches identified epitopes within *S. pneumoniae* PspA with a high degree of identity to those recognized by mAb 4F11 in *P. carinii*. The group of epitopes recognized by mAb 4F11 are not identical, but are highly similar in their proline and positively charged amino acid content. Analysis of the deduced amino acid sequences of the two *P. carinii* antigens containing epitopes recognized by mAb 4F11 suggests that at least one of the two antigens is surface localized. This is in agreement with the IFA data using non-permeabilized *P. carinii* organisms (FIG. 1). A rat *P. carinii* kexin-like molecule has been reported as localized to the cyst surface (Lugli et al., "Cell Surface Protease PRT1 Identified in the Fungal Pathogen *Pneumocystis carinii*," *Mol. Microbiol.* 31:1723-1733 (1999), which is hereby incorporated by reference in its entirety). If *P. carinii* Kex1 and the A12 antigen are on the surface of the organism, the proline rich domains of these molecules would likely be cyst wall-associated based on the proximity of these domains to the hydrophobic C-termini of each protein. The potential for mAb 4F11 to recognize multiple, similar epitopes may explain its ability to recognize *P. carinii* isolated from a number of different hosts. This may also explain the apparent abundance of *P. carinii* surface antigens recognized by 4F11 by IFA.

The initial characterization of mouse *P. carinii* cDNA clone A12 is also identified above. Southern blotting shows a single band recognized by an A12 probe in restriction endonuclease digests of *P. carinii*-infected mouse lung homogenates and no bands in digests of DNA from uninfected mouse lung homogenates, providing further confirmation that A12 is a *P. carinii* antigen. Cloning of the full length A12 nucleic acid and the full length protein encoded thereby will be obtained using the procedures described in Example 9 below, and antigenic characterization of the full length protein will be carried out in the manner described above for characterization of *P. carinii* kexin and the partial sequence of clone A12.

With the identification of the polypeptide fragment encoded by cDNA A12, a total of three mouse *P. carinii* antigens with proline-rich regions have been identified, including *P. carinii* Kex1 and gpA (Haidaris et al., "Molecular Characterization of Mouse *Pneumocystis carinii* Surface Glycoprotein A," *DNA Res.* 5:77-85 (1998); Lee et al., "Molecular Characterization of KEX1, a Kexin-Like Protease in Mouse *Pneumocystis carinii*," *Gene* 242:141-150 (2000), each of which is hereby incorporated by reference in its entirety). However, mAb 4F11 does not bind to gpA (Lee et al., "Molecular Characterization of KEX1, a Kexin-Like Protease in Mouse *Pneumocystis carinii*," *Gene* 242:141-150 (2000)). The proline rich domains of these molecules may represent a conserved motif in *P. carinii* surface antigens. Proline-rich surface proteins have also been identified in the fungi *Candida albicans* (Staab et al., "Developmental Expression of a Tandemly Repeated, Proline- and Glutamine-Rich Amino Acid Motif on Hyphal Surfaces on *Candida albicans*," *J. Biol. Chem.* 271:6298-6305 (1996), which is hereby incorporated by reference in its entirety) and *Saccharomyces cerevisiae* (Frevert et al., "*Saccharomyces cerevisiae* Structural Cell Wall Mannoprotein," *Biochemistry* 24:753-759 (1985), which is hereby incorporated by reference in its entirety), and in a number of gram-positive cocci (Briles et al., "Role of Pneumococcal Surface Protein A in the Virulence of *Streptococcus pneumoniae*," *Rev. Infect. Dis.* 10 Suppl 2:S372-S374 (1988); Fahnestock et al., "Gene for an Immunoglobulin-Binding Protein from a Group G *Streptococcus*,"

J. Bacteriol. 167:870-880 (1986); Guss et al., "Region X, the Cell-Wall-Attachment Part of Staphylococcal Protein A," Eur. J. Biochem. 138:413-420 (1984); Hollingshead et al., "Complete Nucleotide Sequence of Type 6 M Protein of the Group A Streptococcus: Repetitive Structure and Membrane Anchor," J. Biol. Chem. 261:1677-1686 (1986), each of which is hereby incorporated by reference in its entirety). Some of these proline-rich regions are speculated to be cell wall-associated (Guss et al., "Region X, the Cell-Wall-Attachment Part of Staphylococcal Protein A," Eur. J. Biochem. 138:413-420 (1984); Hollingshead et al., "Complete Nucleotide Sequence of Type 6 M Protein of the Group A Streptococcus: Repetitive Structure and Membrane Anchor," J. Biol. Chem. 261:1677-1686 (1986); Lugli et al., "Cell Surface Protease PRT1 Identified in the Fungal Pathogen Pneumocystis carinii," Mol. Microbiol. 31:1723-1733 (1999); Pancholi et al., "Isolation and Characterization of the Cell-Associated Region of Group A Streptococcal M6 Protein," J. Bacteriol. 170:2618-2624 (1988), each of which is hereby incorporated by reference in its entirety).

The recognition of recombinant A12 and mAb 4F11 immunopurified P. carinii antigens by hyperimmune sera demonstrates that antibodies are generated against these molecules in an anti-P. carinii response that is protective (Harmsen et al., "Active Immunity to Pneumocystis carinii Reinfection in T-cell-depleted Mice," Infect. Immun. 63:2391-2395 (1995), which is hereby incorporated by reference in its entirety). The culmination of these points and the ability of mAb 4F11 to confer passive protection against PCP (see Giliotti et al., "Passive Intranasal Monoclonal Antibody Prophylaxis Against Murine Pneumocystis carinii Pneumonia," Infection and Immun. 70(3):1069-1074 (2002), which is hereby incorporated by reference in its entirety) make the P. carinii antigens recognized by mAb 4F11 attractive vaccine candidates.

To determine that protection afforded by mAb 4F11 was due to specific effector activity resulting from antibody binding and not due to merely putting an adhesive protein on the surface of P. carinii, the above-noted passive immunoprophylaxis experiment was repeated using Fab2 fragments of mAb 4F11. These fragments still bound to P. carinii, but because they lacked their Fc portion they could not fix complement or act as an opsonin for phagocytes. Protection from the Fab2 preparation was reduced by 93% when compared to intact mAb 4F11 despite the fact that significantly more Fab2 molecules were administered. This further supports the belief that the P. carinii antigens recognized by mAb 4F11 are attractive vaccine candidates.

In silico analysis identified S. pneumoniae PspA as having a region of similarity to the P. carinii mAb 4F11 epitope. This study confirms the presence of shared surface antigen epitopes between these two highly divergent pathogens. The importance of PspA as a S. pneumoniae antigen has been demonstrated by the ability of immunization of mice with PspA to induce cross-protection against multiple S. pneumoniae strains (McDaniel et al., "PspA, a Surface Protein of Streptococcus pneumoniae, is Capable of Eliciting Protection Against Pneumococci of More than One Capsular Type," Infect. Immun. 59:222-228 (1991); Ralph et al., "Cross-Reactive Protection Eliciting Epitopes of Pneumococcal Surface Protein A," Ann. NY Acad. Sci. 730:361-363 (1994); Tart et al., "Truncated Streptococcus pneumoniae PspA Molecules Elicit Cross-Protective Immunity Against Pneumococcal Challenge in Mice," J. Infect. Dis. 173:380-386 (1996), each of which is hereby incorporated by reference in its entirety). Comparison of the clade defining region of URSP2 PspA to an alignment of a number of different PspA isoforms (Hollingshead et al., "Diversity of PspA: Mosaic Genes and Evidence for Past Recombination in Streptococcus pneumoniae," Infect. Immun. 68:5889-5900 (2000), which is hereby incorporated by reference in its entirety) placed URSP2 PspA in family 1, clade 1. Approximately 50% of S. pneunoniae isolates carry PspA from family 1 (Hollingshead et al., "Diversity of PspA: Mosaic Genes and Evidence for Past Recombination in Streptococcus pneumoniae," Infect. Immun. 68:5889-5900 (2000), which is hereby incorporated by reference in its entirety), suggesting that S. pneumoniae URSP2 PspA represents a potentially prevalent isoform of the molecule. The proline rich region of PspA contains at least one protective epitope since antibodies that react with the proline-rich region of PspA confer cross-protection against multiple S. pneumoniae strains in a mouse model (Brooks-Walter et al., "The pspC Gene of Streptococcus pneumoniae Encodes a Polymorphic Protein, PspC, Which Elicits Cross-Reactive Antibodies to PspA and Provides Immunity to Pneumococcal Bacteremia," Infect. Immun. 67:6533-6542 (1999), which is hereby incorporated by reference in its entirety). Example 8 (above) demonstrated that mice administered mAb 4F11(G1) intraperitoneally prior to intranasal challenge with S. pneumoniae showed a 99.9% reduction in bacteremia compared to control animals as determined by blood cfu counts one day post challenge. In addition, truncated PspA fragments containing the α-helical domain of the molecule, the clade-defining region and the proline-rich repeat region show increased cross-protective capabilities over fragments containing the α-helical domain and clade defining region alone (Ralph et al., "Cross-Reactive Protection Eliciting Epitopes of Pneumococcal Surface Protein A," Ann. NY Acad. Sci. 730:361-363 (1994), which is hereby incorporated by reference in its entirety). Human sera often contain natural, polyreactive antibodies that recognize proline-rich epitopes; these antibodies may represent early defense mechanisms against pathogens (Tchernychev et al., "The Epitopes for Natural Polyreactive Antibodies are Rich in Proline," Proc. Natl. Acad. Sci. USA 94:6335-6339 (1997), which is hereby incorporated by reference in its entirety). Together, these data suggest that exposed proline-rich regions of surface antigens may represent pathogen-associated molecular patterns that are recognized by the immune system (Janeway, Jr., "Approaching the Asymptote? Evolution and Revolution in Immunology," Cold Spring Harb. Symp. Quant. Biol. 54(1):1-13 (1989), which is hereby incorporated by reference in its entirety).

MAb recognition of multiple, proline-rich epitopes, coupled with the prevalence of proline-rich surface antigens on pathogens as different as P. carinii and S. pneumoniae, suggests that it is possible to generate cross-protection by immunization with one or more of these antigens. Such an approach may be of particular interest in prevention of PCP, since P. carinii cannot be grown continuously in culture and organisms derived from one animal host do not provide protection against P. carinii in different host (Gigliotti et al., "Pneumocystis carinii Host Origin Defines the Antibody Specificity and Protective Response Induced by Immunization," J. Infect. Dis. 176:1322-1326 (1997), which is hereby incorporated by reference in its entirety). It will also be of interest to determine whether sera generated against polypeptides containing the mAb 4F11 epitopes are capable of recognizing P. carinii derived from multiple hosts, including humans, as shown for mAb 4F11.

Example 9

Cloning and Sequencing the Complete Open Reading Frame of the cDNA Corresponding to Clone A12

A search of the available databases demonstrated that the regions of the A12 polypeptide flanking the proline-rich region have no ortholog in either P. carinii or other organisms. This suggests that A12 is not part of a large gene family, such as those encoding gpA, where cDNAs are often similar but not identical. Rather, it is likely to be encoded by a single gene, like KEX1, or a relatively small number of paralogous genes. Determining copy number of the A12 gene has implications for the cloning of the full-length cDNA. Two complementary approaches will be used to determine A12 gene copy number: Southern blotting and real time PCR.

For Southern blotting, genomic DNA isolated from *P. carinii* infected mouse lung will be digested with EcoRI, BamHI and HindIII, respectively. Other restriction enzymes will be utilized as necessary. Ten to twenty micrograms of DNA from each digest will be separated by agarose gel electrophoresis, transferred to nitrocellulose filters, and probed with the A12 cDNA. The A12 cDNA will be labeled non-isotopically using biotinylated nucleotides and random octamers as primers with the New England Biolabs Phototope kit (Beverly, Mass.). Hybridization will be performed at high stringency, with the final wash of the blot in 0.1×SSC, 0.1% SDS at 68° C. for 15 min. Hybridization will be detected by binding of enzyme-conjugated avidin to the biotinylated probe. Enhanced chemiluminescence generated using developer solution per the manufacturer's instructions (New England Biolabs Phototope Detection Kit) will be detected by exposure of the filters to film. The homologous clone will be used as the positive control in each hybridization, and genomic DNA from uninfected mouse lung will be used as the negative control.

Genome copy number will be determined as previously described for KEX1 (Lee et al., "Molecular Characterization of KEX1, a Kexin-Like Protease in Mouse *Pneumocystis carinii*," *Gene* 242:141-150 (2000), which is hereby incorporated by reference in its entirety). It is predicted that probing of genomic DNA digested with different enzymes will yield a single band if the A12 gene is single-copy. If some digests yield a single band, and others yield two or more bands, this would suggest a single copy gene with a restriction site for the enzyme in question within the gene or an intron, as seen with EcoRI and KEX1. If such a result is obtained, the genomic copy of A12 will be amplified by PCR and digested with the relevant enzyme to confirm the result. If multiple fragments of sizes sufficient to encompass the whole gene are detected using different restriction enzymes, this would suggest that A12 is multi-copy. As a complementary assay to evaluate copy number, real time PCR will be performed using KEX1 as a control for a single copy gene.

Northern blotting of poly(A+) RNA isolated from *P. carinii*-infected mouse lungs was used to identify the size of the full-length, steady state transcript encoding the A12 antigen. The existing A12 cDNA clone was used as the probe to perform the Northern blot analysis. A transcript of 3.8 kb was identified. Transcript size will be used as a guideline to determine the size of full-length cDNA, as well as a guide for the primer extension procedure described below.

Primer extension and Rapid Amplification of A12 cDNA Ends (RACE) will be used to obtain the 5' end of the A12 cDNA. The Northern blotting results provided an indication of the size of the full-length cDNA and serve as a guide for cloning the remainder of the fragment by RACE. Candidates for antisense primers residing near the 5' end of the A12 cDNA will be tested by primer extension of poly(A)+ mRNA from *P. carinii*-infected mouse lungs using the same methods published in Lee et al., "Molecular Characterization of KEX1, a Kexin-Like Protease in Mouse *Pneumocystis carinii*," *Gene* 242:141-150 (2000), which is hereby incorporated by reference in its entirety. Once a suitable antisense primer has been identified for primer extension, a 5' RACE kit (Invitrogen/Life Technologies) will be used to amplify the remainder of the A12 cDNA. Automated dideoxy terminator nucleotide sequencing of the cDNA will be performed by the University of Rochester Nucleic Acid Core facility.

The identity of the RT-PCR product obtained by RACE will be confirmed as being of *P. carinii* origin by several criteria. First, the amplified nucleotide sequence would be expected to be AT-rich, in keeping with the *P. carinii* genome. Second, a fragment of the clone upstream of the existing A12 sequence will be used as a probe in Northern blots. The transcript should be present in RNA from *P. carinii*-infected mouse lung but not in normal mouse lung. In addition, the banding patterns in the Northern and Southern blots should be overlapping with those using clone A12. Confirmation of that the 5' end of the cDNA has been cloned will be obtained using primer extension analysis with an antisense oligonucleotide derived from near the 5' end of the new cDNA fragment. The two pieces of the A12 cDNA will then be assembled into a contiguous cDNA using splice-overlap PCR.

Southern blots of genomic DNA using the newly identified cDNA fragment should hybridize to the same fragments in *P. carinii*-infected mouse lung as does clone A12, but no hybridization to genomic DNA from normal mouse lung should be observed. If additional bands are seen in the Southern blot compared to those obtained with the A12 probe, it could indicate that additional copies of the gene are present in the genome. If Southern blotting indicates that multiple copies of the gene are present, assembly of a consensus sequence will be carried out to define the degree of diversity in the specific gene by sequence analysis of multiple clones.

If the initial RACE strategy is unsuccessful, several alternatives are available for cloning the remainder of the A12 cDNA. First, oligonucleotides from regions of A12 outside the proline rich region, which is thought to be unique based on the absence of apparent homology in available databases, will be used to screen an existing cDNA library. This is the same approach that was used to identify the full-length KEX1 cDNA reported in Lee et al., "Molecular Characterization of KEX1, a Kexin-Like Protease in Mouse *Pneumocystis carinii*," *Gene* 242:141-150 (2000), which is hereby incorporated by reference in its entirety). As a second alternative, an additional mab to A12 can be used to screen a cDNA library for full-length sequence, as was done when *P. carinii* gpA was cloned and characterized (Haidaris et al., "Expression and Characterization of a cDNA Clone Encoding an Immunodominant Surface Glycoprotein of *Pneumocystis carinii*," *J. Infect. Dis.* 166:1113-1123 (1992), which is hereby incorporated by reference in its entirety). If a larger clone is found with no apparent start site, the screening and/or the RACE approach will be repeated, with the rationale that obtaining a smaller RT-PCR product may be more successful than using primer extension from the 5' end of the A12 cDNA.

A more complete nucleotide sequence for the open reading frame corresponding to clone A12 has since been obtained. The nucleotide sequence and amino acid sequence of the putative encoded protein are shown in FIGS. 8A-B.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated polypeptide comprising the amino acid sequence of SEQ ID NO: 5.

2. A pharmaceutical composition comprising the isolated polypeptide of claim 1 and a pharmaceutically acceptable carrier.

3. An immunogenic conjugate comprising the isolated polypeptide of claim 1 and a bacterial carrier molecule covalently or non-covalently bound to the polypeptide.

4. A pharmaceutical composition comprising the immunogenic conjugate of claim 3 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,815,918 B2 | Page 1 of 1 |
| APPLICATION NO. | : 10/584871 | |
| DATED | : October 19, 2010 | |
| INVENTOR(S) | : Gigliotti et al. | |

It is certified that error appears in the above-identified patent and that said Letters Patent is hereby corrected as shown below:

At col. 1, lines 12-16, delete:

"The present invention was made, at least in part, with funding received from the National Institutes of Heath under grant numbers AI23302, AI45479, and 5T32AI07362 (NI-AID). The U.S. government may have certain rights in this invention."

and insert

--This invention was made with government support under AI023302, AI045479, and AI007362 awarded by National Institutes of Health. The government has certain rights in the invention.--

Signed and Sealed this
Twenty-seventh Day of March, 2012

David J. Kappos
*Director of the United States Patent and Trademark Office*